(12) United States Patent
Kikuchi et al.

(10) Patent No.: US 10,729,851 B2
(45) Date of Patent: Aug. 4, 2020

(54) PHARMACEUTICAL INJECTION DEVICE

(71) Applicant: PHC Holdings Corporation, Minato-ku, Tokyo (JP)

(72) Inventors: Seiji Kikuchi, Ehime (JP); Toshiaki Iio, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 249 days.

(21) Appl. No.: 15/100,342

(22) PCT Filed: Nov. 28, 2014

(86) PCT No.: PCT/JP2014/081638
§ 371 (c)(1),
(2) Date: May 31, 2016

(87) PCT Pub. No.: WO2015/098430
PCT Pub. Date: Jul. 2, 2015

(65) Prior Publication Data
US 2016/0296700 A1  Oct. 13, 2016

(30) Foreign Application Priority Data

Dec. 27, 2013 (JP) .................................. 2013-273243
Jan. 17, 2014 (JP) .................................. 2014-006466

(51) Int. Cl.
*A61M 5/20* (2006.01)
*A61M 5/32* (2006.01)
(Continued)

(52) U.S. Cl.
CPC .......... *A61M 5/20* (2013.01); *A61M 5/31566* (2013.01); *A61M 5/31576* (2013.01);
(Continued)

(58) Field of Classification Search
CPC ................ A61M 5/20; A61M 5/31566; A61M 5/31576; A61M 5/3205; A61M 5/34;
(Continued)

(56) References Cited

U.S. PATENT DOCUMENTS 6,290,683 B1  9/2001  Erez et al.
7,704,231 B2  4/2010  Pongpairochana et al.
(Continued)

FOREIGN PATENT DOCUMENTS

JP  2005-245852 A  9/2005
JP  2007-522853 A  8/2007
(Continued)

OTHER PUBLICATIONS

Internationanl Search Report of corresponding PCT Application No. PCT/JP2014/081638 dated Feb. 10, 2015.
(Continued)

*Primary Examiner* — Kevin C Sirmons
*Assistant Examiner* — Tezita Z Watts
(74) *Attorney, Agent, or Firm* — Wenderoth, Lind & Ponack, L.L.P.

(57) ABSTRACT

With certain implementations, the configuration is such that a controller uses a first driver to move a pharmaceutical syringe attachment component closer to the distal end side than a needle removal position when a needle unit is attached to a pharmaceutical syringe unit or when the needle unit is removed from the pharmaceutical syringe unit, so when an injection needle is attached to the pharmaceutical syringe unit, or when the injection needle is removed from the pharmaceutical syringe unit, these operations can be executed without removing a distal end cap, which makes the device extremely convenient to use.

15 Claims, 41 Drawing Sheets

(51) Int. Cl.
*A61M 5/34* (2006.01)
*A61M 5/36* (2006.01)
*A61M 5/315* (2006.01)
*A61M 5/24* (2006.01)
*A61M 5/31* (2006.01)

(52) U.S. Cl.
CPC ............ *A61M 5/3205* (2013.01); *A61M 5/34* (2013.01); *A61M 5/36* (2013.01); *A61M 5/24* (2013.01); *A61M 5/3146* (2013.01); *A61M 5/3202* (2013.01); *A61M 2005/206* (2013.01); *A61M 2005/31588* (2013.01); *A61M 2205/14* (2013.01); *A61M 2205/16* (2013.01); *A61M 2205/50* (2013.01); *A61M 2205/502* (2013.01)

(58) Field of Classification Search
CPC ........ A61M 5/36; A61M 5/24; A61M 5/3146; A61M 5/3202; A61M 2005/206; A61M 2005/31588; A61M 2205/14; A61M 2205/16; A61M 2205/50; A61M 2205/502
See application file for complete search history.

(56) References Cited

U.S. PATENT DOCUMENTS

| | | |
|---|---|---|
| 2003/0083626 A1 | 5/2003 | Munk et al. |
| 2005/0197650 A1 | 9/2005 | Sugimoto et al. |
| 2007/0197968 A1 | 8/2007 | Pongpairochana et al. |
| 2009/0054832 A1 | 2/2009 | Sugimoto et al. |
| 2009/0062777 A1 | 3/2009 | Sugimoto et al. |
| 2010/0160857 A1 | 6/2010 | Pongpairochana et al. |
| 2011/0004165 A1* | 1/2011 | Iio ............ A61M 5/24 604/197 |
| 2011/0201998 A1 | 8/2011 | Pongpairochana et al. |
| 2011/0224616 A1 | 9/2011 | Slate et al. |
| 2011/0257602 A1* | 10/2011 | Watanabe ........ A61M 5/20 604/189 |
| 2012/0101439 A9 | 4/2012 | Slate et al. |
| 2012/0323176 A1* | 12/2012 | Watanabe ........ A61M 5/20 604/131 |
| 2013/0172819 A1 | 7/2013 | Iio et al. |
| 2014/0012229 A1* | 1/2014 | Bokelman ........ A61M 5/2033 604/506 |
| 2014/0330215 A1 | 11/2014 | Kikuchi et al. |
| 2014/0371683 A1 | 12/2014 | Iio et al. |
| 2015/0174324 A1 | 6/2015 | Wurmbauer et al. |
| 2015/0374912 A1 | 12/2015 | Sugimoto et al. |

FOREIGN PATENT DOCUMENTS

| | | |
|---|---|---|
| JP | 2011-520569 A | 7/2011 |
| JP | 2013-090977 A | 5/2013 |
| WO | 2009/125582 A1 | 10/2009 |
| WO | 2009/143255 A1 | 11/2009 |
| WO | 2010/100883 | 9/2010 |
| WO | 2012/066767 A1 | 5/2012 |
| WO | 2013/079643 | 6/2013 |
| WO | 2013/084505 A1 | 6/2013 |
| WO | 2013186619 A1 | 12/2013 |

OTHER PUBLICATIONS

The European Search Report from the corresponding Europan Patent Application No. 14874844.5 dated Nov. 23, 2016.

* cited by examiner

US 10,729,851 B2

PHARMACEUTICAL INJECTION DEVICE

PRIORITY

This is a National Stage Application under 35 U.S.C. § 365 of International Application PCT/JP2014/081638, with an international filing date of Nov. 28, 2014, which claims priority to Japanese Patent Application No. 2013-273243 filed on Dec. 27, 2013 and Japanese Patent Application No. 2014-006466 filed on Jan. 17, 2014. The entire disclosures of International Application PCT/JP2014/081638, Japanese Patent Application No. 2013-273243 and Japanese Patent Application No. 2014-006466 are hereby incorporated herein by reference.

TECHNICAL FIELD

Certain implementations relate to a pharmaceutical injection device for injecting a pharmaceutical into a human body, etc.

BACKGROUND

A conventional pharmaceutical injection device of this type was configured to comprise a main body case having a pharmaceutical syringe attachment component on its distal end side, a distal end cap removably attached to the distal end side of the main body case, a first driver that moves a pharmaceutical syringe unit attached to the pharmaceutical syringe attachment component to the distal end side or the rear side within the distal end cap, a second driver that moves a gasket of a pharmaceutical syringe constituting the pharmaceutical syringe unit to the distal end side, and a controller that is connected to the first and second drivers.

Another conventional pharmaceutical injection device of this type was configured to comprise a main body case having a pharmaceutical syringe attachment component on its distal end side, a distal end cap removably attached to the distal end side of the main body case, a first driver that moves a pharmaceutical syringe unit attached to the pharmaceutical syringe attachment component to the distal end side or the rear side, a second driver that moves a gasket of a pharmaceutical syringe constituting the pharmaceutical syringe unit to the distal end side, and a controller that is connected to the first and second drivers.

SUMMARY

In the prior art, before the pharmaceutical is injected, first the distal end cap is removed from the main body case, and then the pharmaceutical syringe unit is attached to the pharmaceutical syringe attachment component, after which the needle unit is attached to this pharmaceutical syringe unit. In this state the distal end cap is attached, and then the needle case and needle cap constituting the needle unit are pulled out through the distal end opening of the distal end cap.

In this state the distal end cap is pressed against the skin, the first driver then causes the needle to pierce the skin, the pharmaceutical in the pharmaceutical syringe is injected into the body by the second driver, and after this the needle is pulled out by the first driver.

After the pharmaceutical injection, first the needle case is attached to the needle from the distal end opening in the distal end cap, and then the distal end cap is removed from the main body case, after which the needle unit to which the needle cap is not attached is removed from the pharmaceutical syringe unit.

When needs to be improved here is convenience of use.

Specifically, depending on the type of pharmaceutical in the pharmaceutical syringe constituting the pharmaceutical syringe unit, if the pharmaceutical syringe is attached all at once to the pharmaceutical syringe attachment component, it remains attached to the pharmaceutical syringe attachment component until the pharmaceutical is used up.

That is, depending on the type of pharmaceutical, the distal end cap should be removed from the main body case only when the pharmaceutical syringe unit is being attached to or removed from the pharmaceutical syringe attachment component. Conventionally, however, the distal end cap was removed from the main body case even during the attachment of the needle unit to the pharmaceutical syringe unit, during removal of the needle unit from the pharmaceutical syringe unit, etc., and this distal end cap had to be replaced, which means that convenience was not as good as it could be.

In view of this, it is an object of certain implementations to reduce removal of the distal end cap to make the device more convenient to use.

Also, in the prior art, the distal end cap is attached to the main body case, and in this state the distal end cap is pressed against the skin, and then the pharmaceutical syringe unit is moved to the distal end side by the first driver, which pierces the skin with the pharmaceutical injection needle attached to the distal end of the pharmaceutical syringe unit.

After this, the second driver moves the gasket of the pharmaceutical syringe to the distal end side, and the pharmaceutical inside the pharmaceutical syringe is injected through the injection needle and into the body.

That is, the distal end cap also functions as a skin pad, before injection, and the injection needle is covered with this distal end cap, which prevents accidents from being caused by the injection needle. The distal end cap is therefore an extremely useful part.

Nevertheless, if the distal end cap should be lost, the detector will detect that it is not attached to the main body case, and as a result the operation of actuating the first and second drivers and injecting the pharmaceutical cannot be executed.

Also, when the distal end cap is attached, if the first driver should malfunction, the injection needle cannot be pushed out to the distal end side of the distal end cap, and here again the pharmaceutical injection operation cannot be executed.

In view of this, it is an object of certain implementations to provide a pharmaceutical injection device with which pharmaceutical injection will be possible even if some sort of trouble should occur in the components that assist in pharmaceutical injection, such as when the distal end cap is lost, or when the first driver malfunctions.

To achieve the stated object, the pharmaceutical injection device of the first implementation may comprise a main body case having a pharmaceutical syringe attachment component on its distal end side, a distal end cap removably attached to the distal end side of the main body case, a first driver that moves a pharmaceutical syringe unit attached to the pharmaceutical syringe attachment component to the distal end side or the rear side, a second driver that moves a gasket of a pharmaceutical syringe constituting the pharmaceutical syringe unit to the distal end side, and a controller that is connected to the first driver and the second driver, wherein the controller is configured so that the pharmaceutical syringe attachment component is moved to a needle operation position that is closer to the distal end side than the needle removal position when an injection needle is attached to the pharmaceutical syringe unit, or when the injection needle is removed from the pharmaceutical syringe unit.

Specifically, the controller may be configured to use the first driver to move the pharmaceutical syringe attachment component to a needle operation position that is closer to the distal end side than the needle removal position when the injection needle is attached to the pharmaceutical syringe unit or when the injection needle is removed from the pharmaceutical syringe unit, so even if the distal end cap is removed from the main body case during attachment of the injection needle to the pharmaceutical syringe unit or during removal of the injection needle from the pharmaceutical syringe unit, these operations can still be executed, making the device extremely easy to use.

The pharmaceutical injection device of the second implementation may comprise a main body case having a pharmaceutical syringe attachment component on its distal end side, a distal end cap that can be removably attached to the distal end side of the main body case, a first driver that moves a pharmaceutical syringe unit attached to the pharmaceutical syringe attachment component to the distal end side or the rear side within the distal end cap, a second driver that moves a gasket of a pharmaceutical syringe constituting the pharmaceutical syringe unit to the distal end side, an attached state detector that detects the attached state of the distal end cap to the main body case, and a controller that, during pharmaceutical injection, can execute a normal pharmaceutical injection mode in which the first and second drivers are actuated when the attached state detector has detected a state in which the distal end cap has been attached to the main body case, and can execute a simple pharmaceutical injection mode in which only the second driver is actuated when the attached state detector has detected a state in which the distal end cap has not been attached to the main body case.

Specifically, the controller may be configured to be able to execute a normal pharmaceutical injection mode in which the first and second drivers are actuated after the attached state detector has detected the mounting of the distal end cap to the main body case, and a simple pharmaceutical injection mode in which only the second driver is actuated after the attached state detector has detected the non-attachment of the distal end cap to the main body case.

Therefore, even if the distal end cap should be lost, pharmaceutical injection can still be carried out by executing the simple pharmaceutical injection mode, in which only the second driver is actuated, after the attached state detector has detected the non-attachment of the distal end cap to the main body case. This makes the device extremely convenient to use.

The pharmaceutical injection device of the third implementation may comprise a main body case having a pharmaceutical syringe attachment component on its distal end side, a distal end cap that can be removably attached to the distal end side of the main body case, a first driver that moves a pharmaceutical syringe unit attached to the pharmaceutical syringe attachment component to the distal end side or the rear side, a second driver that moves a gasket of a pharmaceutical syringe constituting the pharmaceutical syringe unit to the distal end side, an operating state detector that detects the operating state of the first driver, and a controller that, during pharmaceutical injection, can execute a simple pharmaceutical injection mode in which only the second driver is actuated when the operating state detector has detected that the first driver is not operating properly.

Consequently, even if the first driver should malfunction, pharmaceutical injection can be carried out by executing the simple pharmaceutical injection mode in which only the second driver is actuated, and this makes the device extremely convenient to use.

As discussed above, pharmaceutical injection can be carried out even when some sort of trouble should occur in the components that assist in pharmaceutical injection, such as the first driver or the distal end cap.

Certain implementations may provide a pharmaceutical injection device with which attachment or removal of the distal end cap is reduced to make the device more convenient to use.

Certain implementations may provide a pharmaceutical injection device with which pharmaceutical injection can be carried out even if some sort of trouble should occur in the components that assist in pharmaceutical injection.

DETAILED DESCRIPTION

An embodiment of the present invention will now be described through reference to the appended drawings.

Embodiment 1

1. Configuration 1-1. Overall Summary of Pharmaceutical Injection Device

Figure 1:
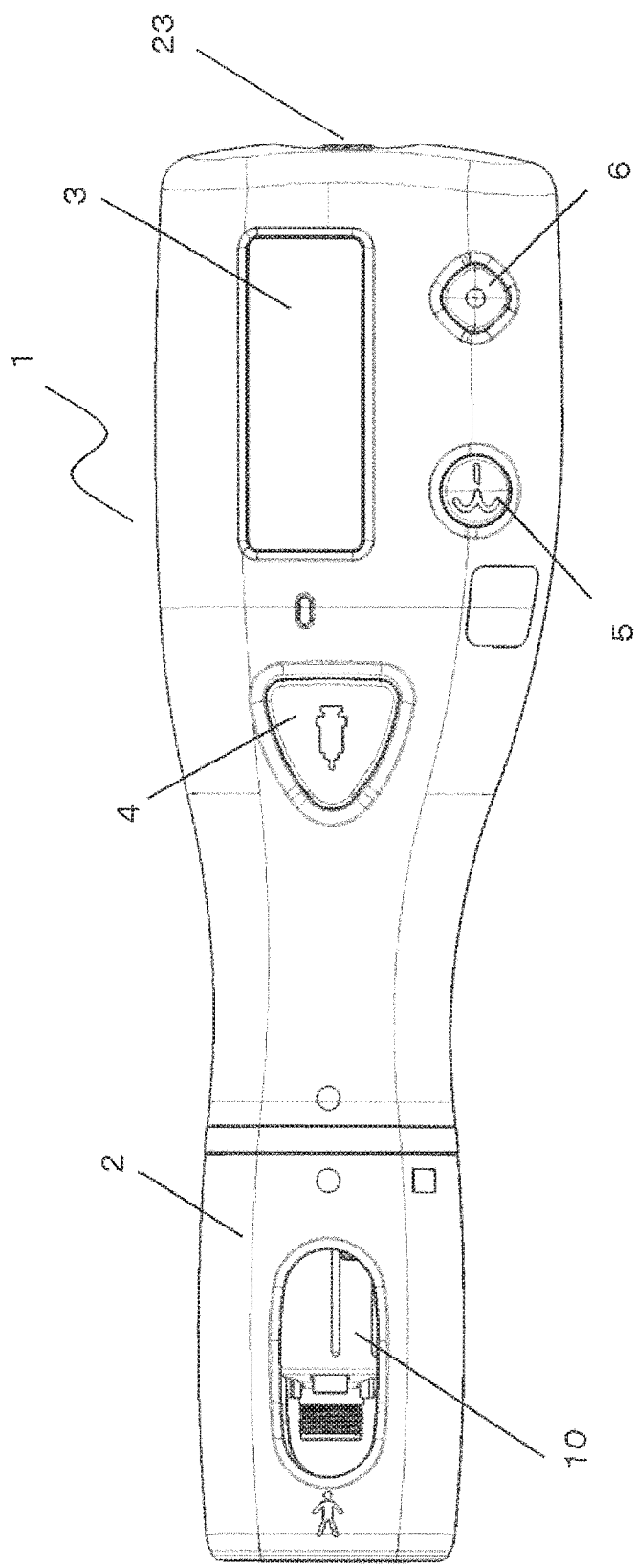
FIG. 1 is a front view of the pharmaceutical injection device pertaining to an embodiment of the present invention.
Figure 2:
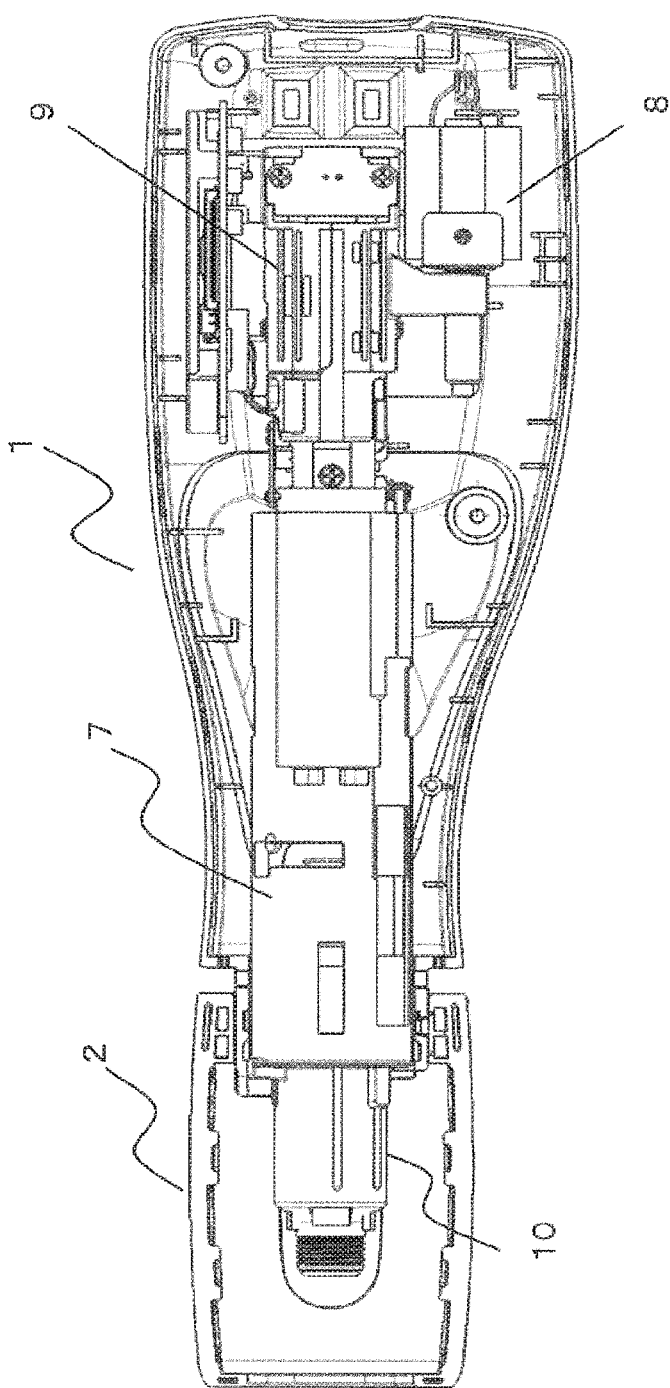
FIG. 2 is a front view of the internal configuration of the pharmaceutical injection device in FIG. 1 (with front cover removed; needle removal position)

In FIGS. 1 and 2, 1 is a main body case, and a distal end cap 2 is removably attached to the distal end side of this main body case 1.

The front of this main body case 1 is provided with a display component 3, an inject button 4, a Yes button 5 to select "Yes" to a question, and a No button 6 to select "No" to a question.

Also, a pharmaceutical syringe attachment component 7, a first driver 8 that moves this pharmaceutical syringe attachment component 7 to the distal end side or rearward from this distal end side, and a second driver 9 that moves a piston 11 (see FIG. 3) to the distal end side to push out the pharmaceutical, are provided inside the main body case 1. The first driver 8 move the second driver to the distal end side or the rear side along with the pharmaceutical syringe attachment component 7.

The term "distal end side" or "front side" here is the distal end cap 2 side (the side on which the injection needle is attached), and "rear end" or "rear side" is the side on which a power button 23 is provided.

A pharmaceutical syringe unit 10 is removably attached to the pharmaceutical syringe attachment component 7.

These components will be described briefly through reference to FIG. 3. When the first driver 8 moves an inner case 12 constituting the pharmaceutical syringe attachment component 7 to the distal end side or the rear side, the pharmaceutical syringe unit 10 mounted inside the inner case 12 also moves to the distal end side or the rear side.

Figure 3:
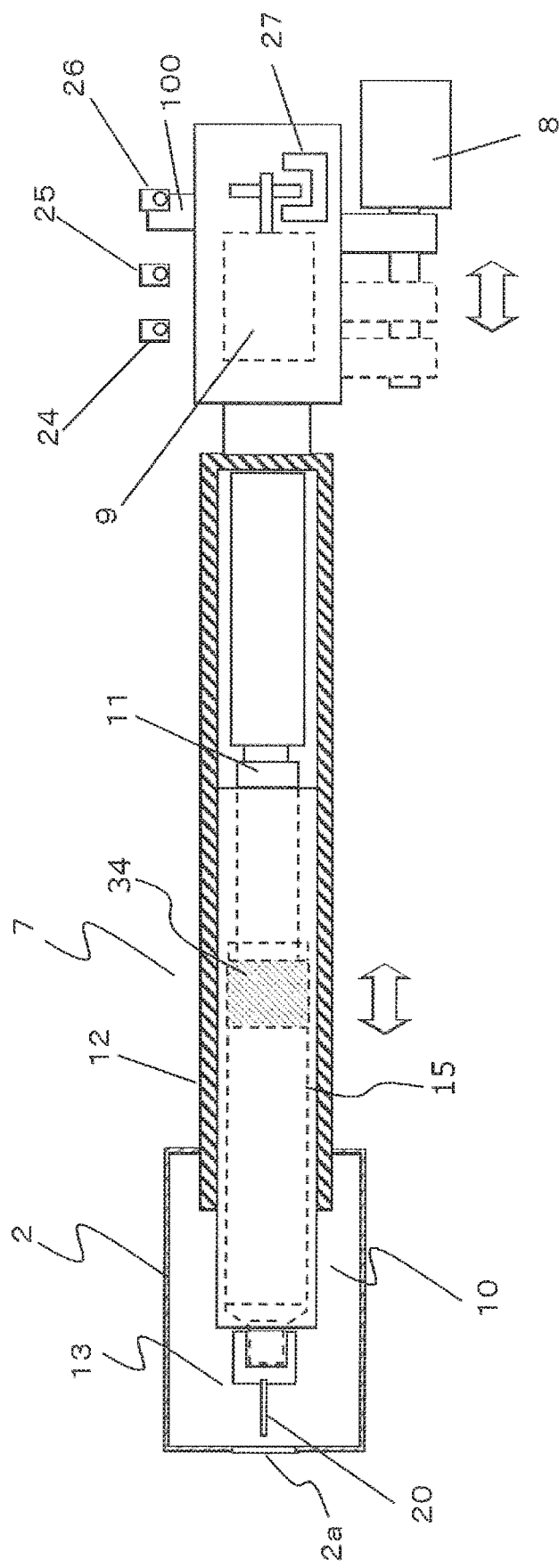
FIG. 3 is a simplified cross section of the pharmaceutical injection device in FIG. 1.

Also, as shown in FIG. 3, since a needle unit 13 is attached to the distal end part of the pharmaceutical syringe unit 10, this needle unit 13 also ends up moving to the distal end side or the rear side.

This state, that is, a state in which the needle unit 13 moves to the distal end side, is a needle insertion state. Conversely, a state in which the needle unit 13 moves to the rear side is a needle removal state.

1-2. Pharmaceutical Syringe Unit 10

The pharmaceutical syringe unit 10 will now be described through reference to FIGS. 4 to 8.

Figure 13:
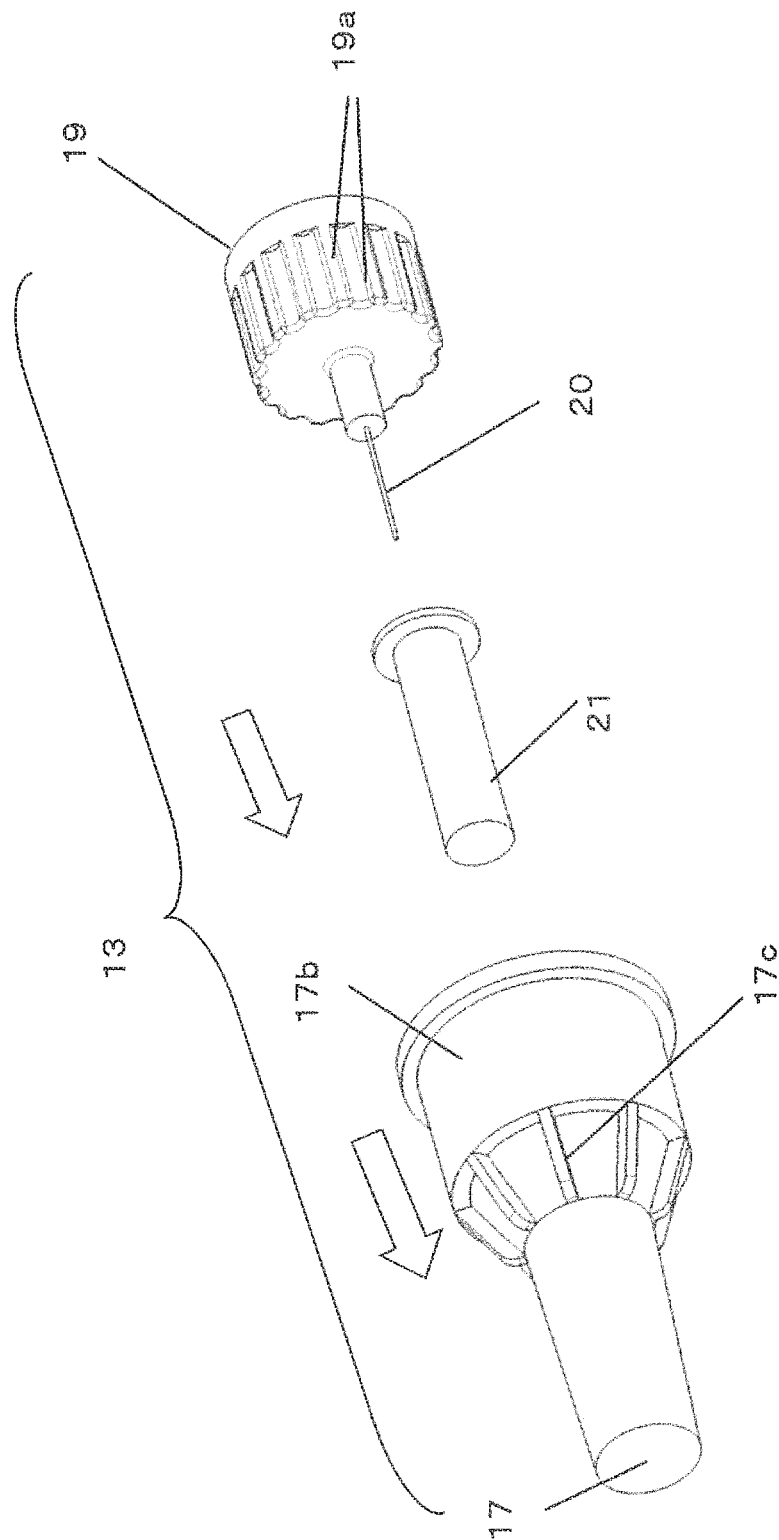
FIG. 13 is an exploded oblique view of the needle unit.

The pharmaceutical syringe unit 10 comprises a syringe cover 14, a pharmaceutical syringe 15 attached in the interior thereof, a first detection member 16 that detects when an injection needle 20 (more precisely, a needle base 19 to which the injection needle 20 is provided; see FIG. 13) constituting the needle unit 13 has been attached on the distal end side of the pharmaceutical syringe 15, and a second detection member 18 that detects when a needle case 17 (see FIG. 13) constituting the needle unit 13 has been attached.

Figure 4:
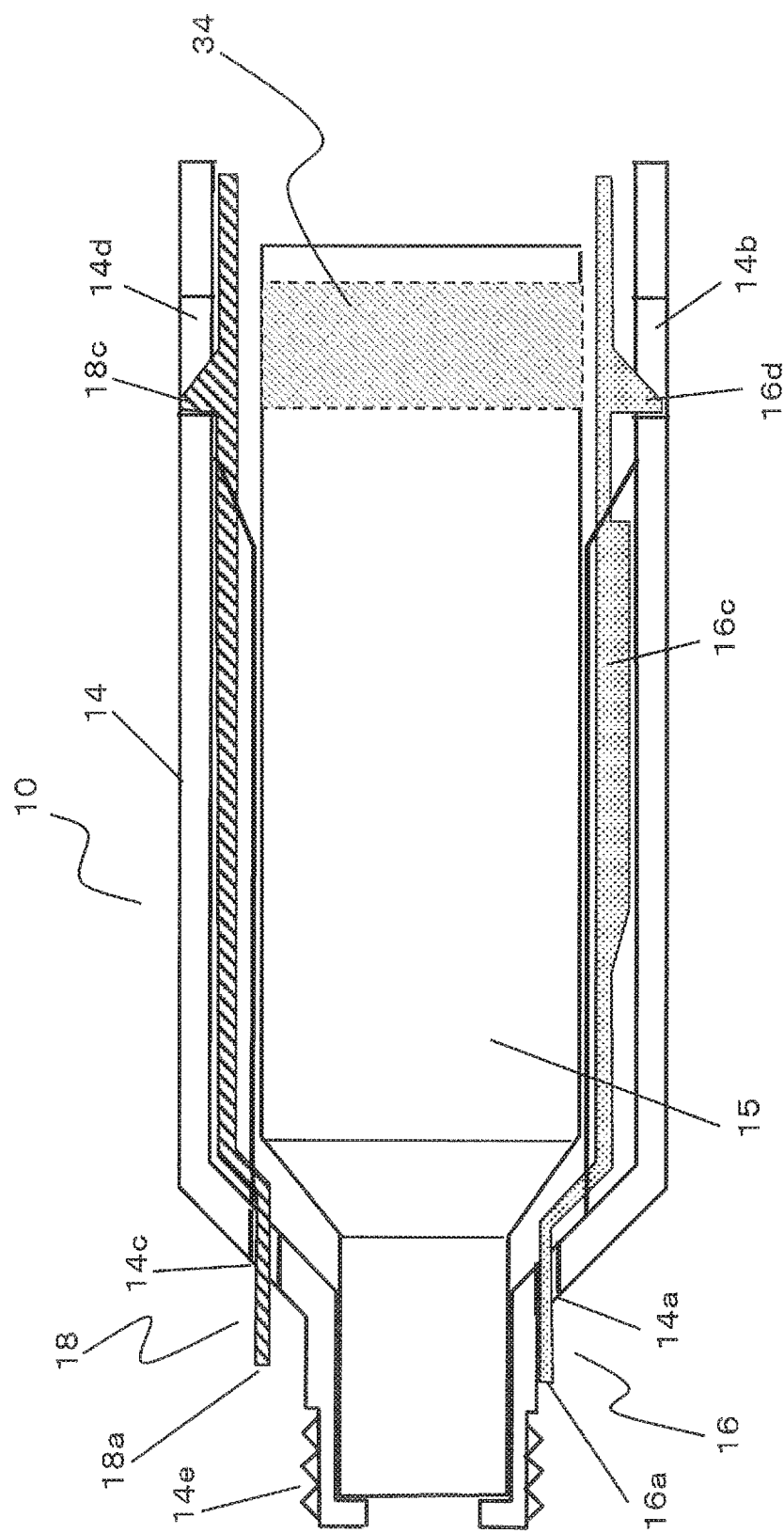
FIG. 4 is a cross section of the main components of the pharmaceutical syringe unit of the pharmaceutical injection device in FIG. 1.

As shown in FIGS. 3 and 4, a gasket 34 is provided to the pharmaceutical syringe 15, and the gasket 34 is moved by the second driver 9 to the distal end side by the piston 11 inserted into the pharmaceutical syringe unit 10. This movement of the gasket 34 causes the pharmaceutical inside the pharmaceutical syringe 15 to come out of the injection needle 20.

Figure 5:
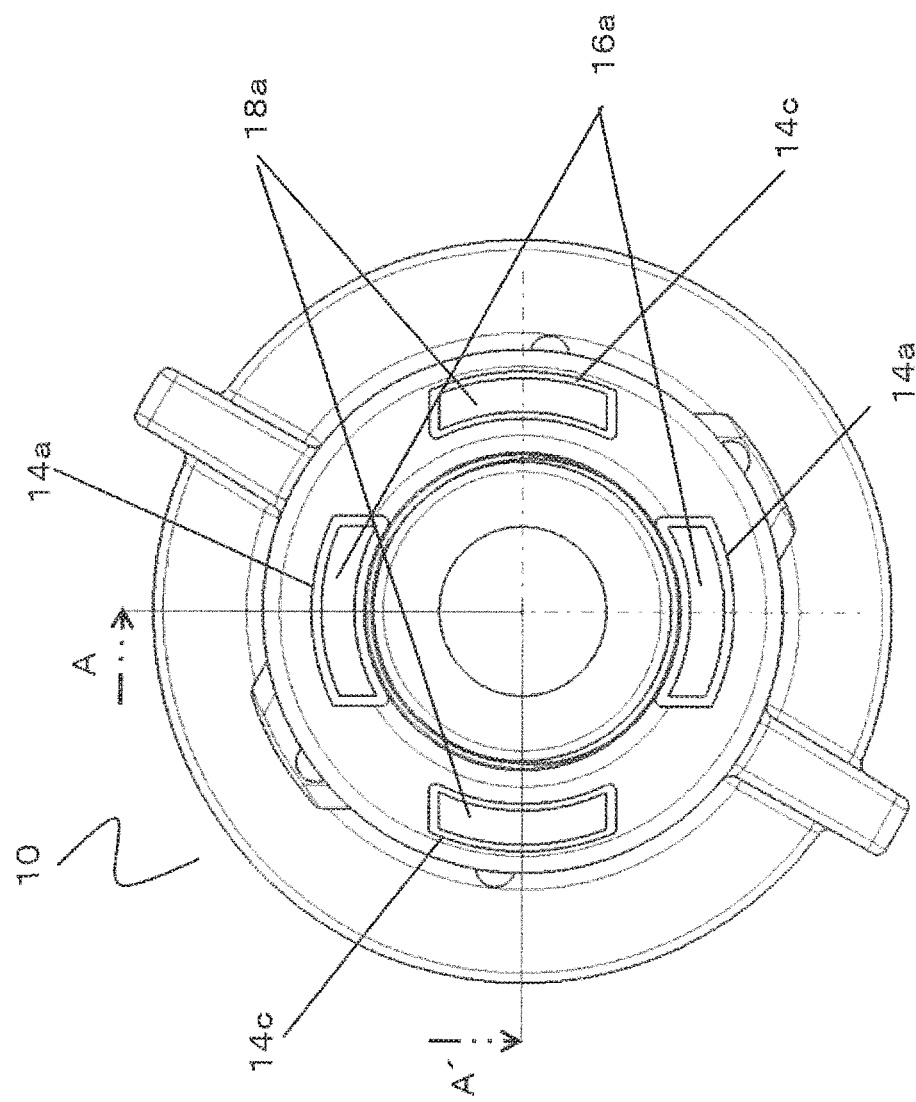
FIG. 5 is a side view as seen from the distal end side in FIG. 4.
Figure 6:
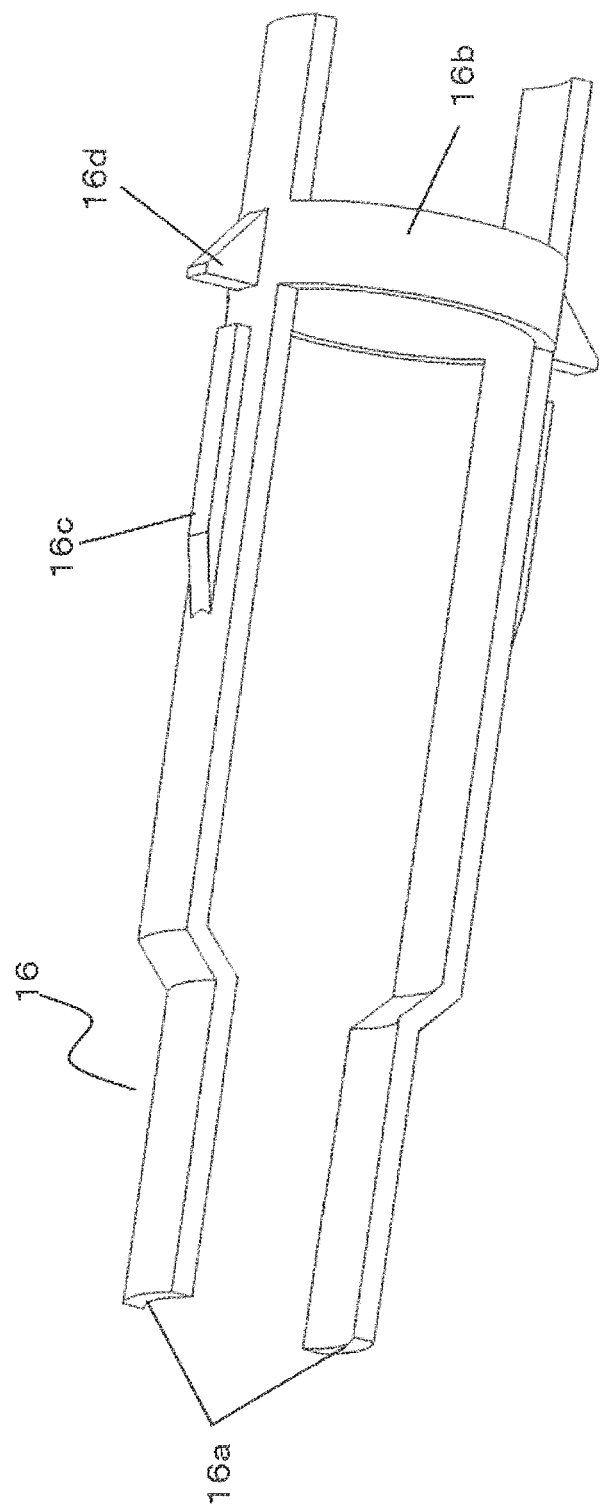
FIG. 6 is an oblique view of a first detection member that constitutes the pharmaceutical syringe unit in FIG. 4.

As shown in FIG. 6, the first detection member 16 has two detector levers 16a. As shown in FIGS. 4 and 5, these detector levers 16a pass through distal end side openings 14a of the syringe cover 14, and extend to the distal end side. FIG. 4 is a cross section along the A'-A line in FIG. 5.

Figure 8:
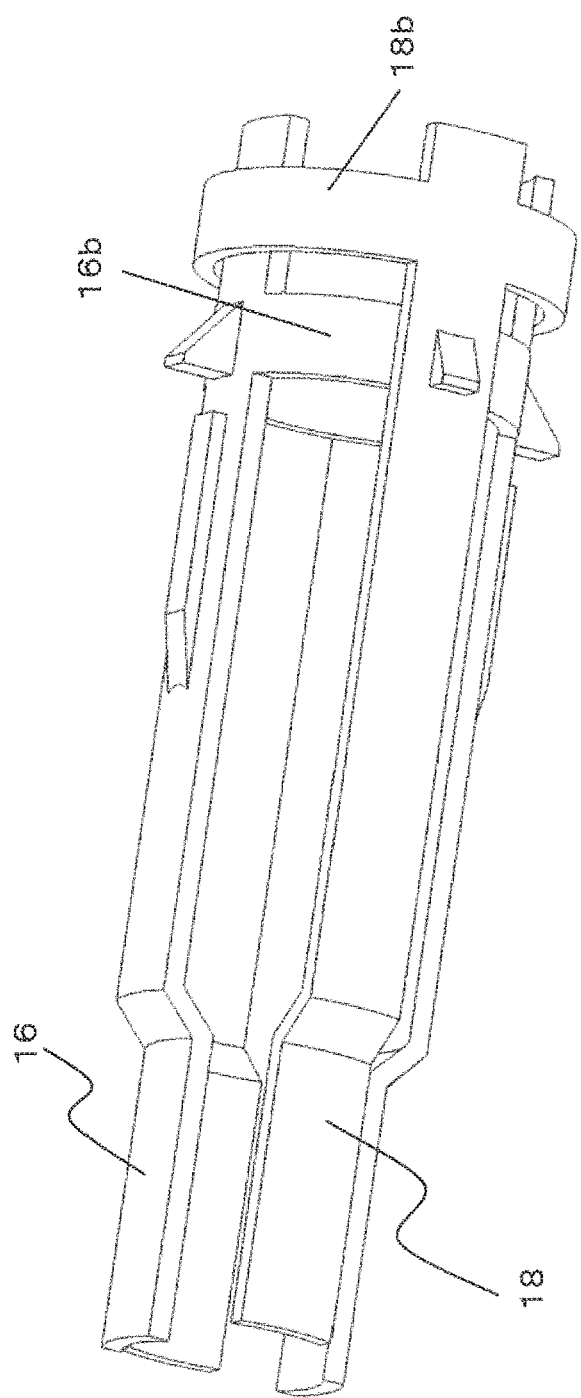
FIG. 8 is an oblique view that combines the first detection member and the second detection member in FIGS. 6 and 7.

As shown in FIGS. 6 and 8, these detector levers 16a are integrally held together on the rear side by an annular part 16b.

As shown in FIG. 6, protrusions 16c are provided on the outer peripheral side of the detector levers 16a, and these protrusions 16c come into contact with the inner walls of the syringe cover 14 as shown in FIG. 4.

Also, protrusions 16*d* are provided to the rear of the protrusions 16*c*. These protrusions 16*d* jut into openings 14*b* of the syringe cover 14.

That is, the pharmaceutical syringe unit 10 is configured such that these protrusions 16*d* prevent the first detection member 16 from moving to the distal end side.

Figure 7:
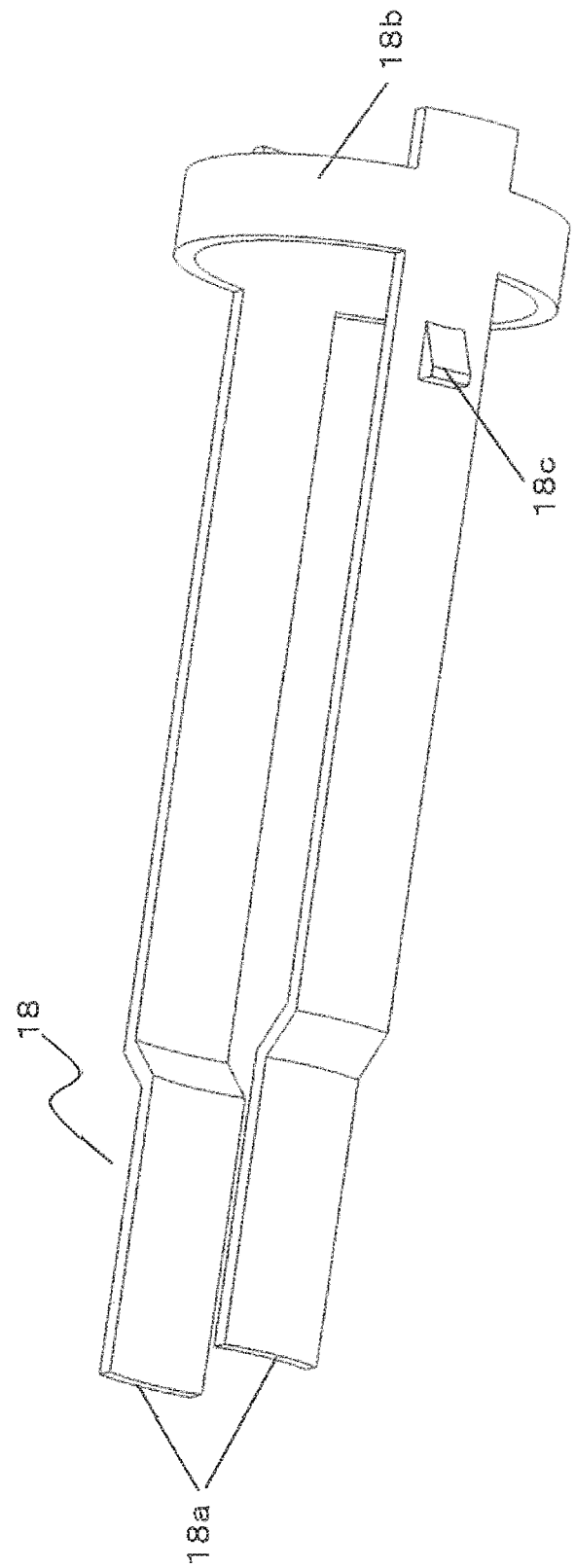
FIG. 7 is an oblique view of a second detection member that constitutes the pharmaceutical syringe unit in FIG. 4.

As shown in FIGS. 7 and 8, the second detection member 18 has two detector levers 18*a*. These detector levers 18*a* pass through distal end side openings 14*c* of the syringe cover 14, and extend to the distal end side.

As shown in FIG. 7, these detector levers 18*a* are integrally held together on the rear side by an annular part 18*b*.

Also, protrusions 18*c* are provided to the detector levers 18*a* on the distal end side of the annular part 18*b*, and these protrusions 18*c* jut into openings 14*d* in the syringe cover 14.

That is, the pharmaceutical syringe unit 10 is configured such that these protrusions 18*c* prevent the second detection member 18 from moving to the distal end side.

The first detection member 16 and the second detection member 18 are biased to the distal end side by a biasing member (not shown) in a state in which the pharmaceutical syringe unit 10 has been attached to the pharmaceutical syringe attachment component 7.

Threads 14*e* are provided around the outer periphery of the distal end of the syringe cover 14 shown in FIG. 4. These threads 14*e* are used to attach and remove the needle unit 13 shown in FIGS. 13 and 14.

1-3. Needle Unit 13

Figure 14:
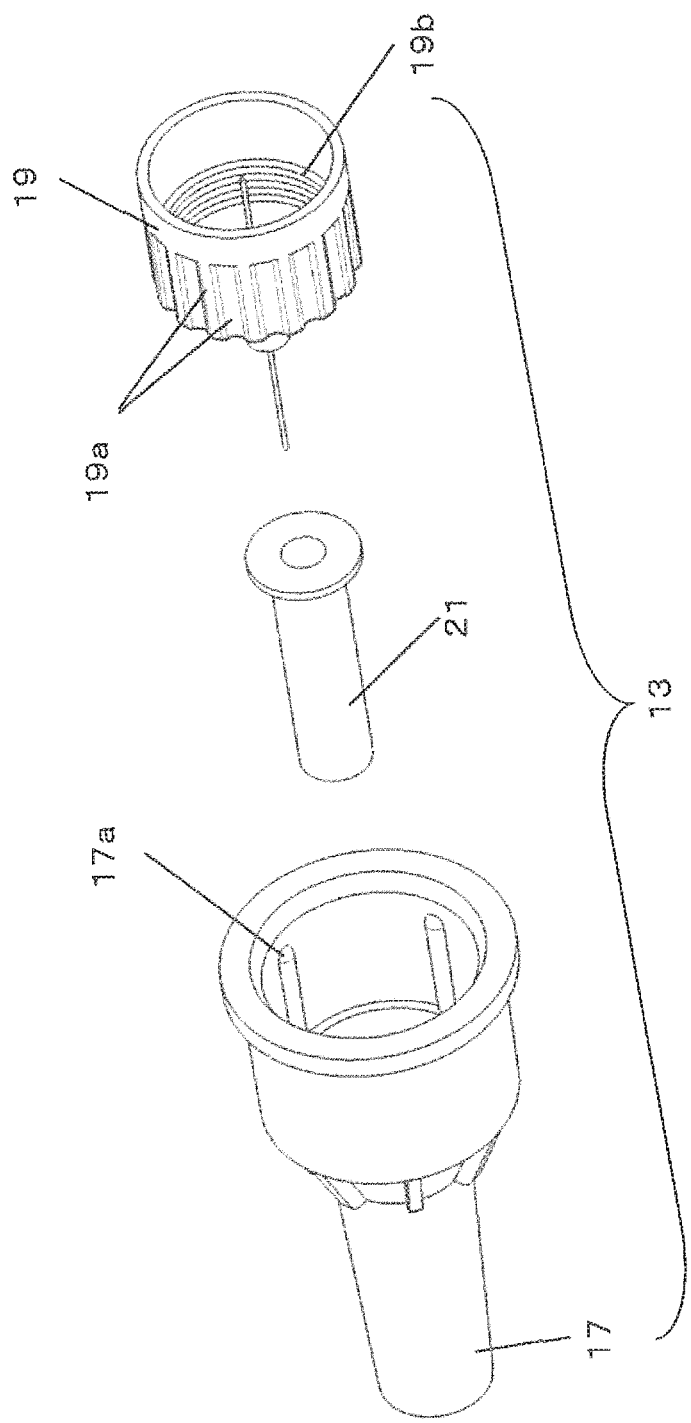
FIG. 14 is an exploded oblique view of the needle unit.

As shown in FIGS. 13 and 14, the needle unit 13 is made up of the injection needle 20, which is implanted in the needle base 19 threaded into the threads 14*e* of the syringe cover 14, a needle cap 21 that is removably attached to the injection needle 20, and the needle case 17 that covers the needle cap 21 and the needle base 19.

Bumps 19*a* that extend rearward from the distal end are provided around the outside of the needle base 19, and threads 19*b* that mesh with the threads 14*e* of the syringe cover 14 are provided around the inside of the needle base 19.

Protrusions 17*a* that engage with the convex parts of the bumps 19*a* of the needle base 19 are provided around the inside on the rear side of the needle case 17. More specifically, these protrusions 17*a* extend from the distal end side toward the rear side, and can be smoothly fitted into the concave parts of the bumps 19*a* of the needle base 19.

In a state in which the protrusions 17*a* have been fitted into the concave parts of the bumps 19*a*, since the protrusions 17*a* of the needle case 17 engage with the bumps 19*a* of the needle base 19, when the needle case 17 is turned, the needle base 19 also turns. This allows the needle unit 13 to be removed from and attached to the syringe cover 14.

When the needle base 19 provided to the injection needle 20 is threaded into the threads 14*e* (see FIG. 4), the first detection member 16 is pushed to the rear by the rear edge of the needle base 19. When the rearward movement of the first detection member 16 is detected by a first detector switch 40 (see FIG. 11) provided to the pharmaceutical syringe attachment component 7, it is detected that the needle base 19 has been attached to the pharmaceutical syringe unit 10. Specifically, it is detected that the injection needle 20 has been attached to the pharmaceutical syringe unit 10. The first detector switch 40 is disposed on the rear side of the first detection member 16 in a state in which the pharmaceutical syringe unit 10 has been attached to the pharmaceutical syringe attachment component 7.

Also, when the needle case 17 is attached to the pharmaceutical syringe unit 10 via the needle base 19, the second detection member 18 is pushed to the rear by the rear edge of the needle case 17. When the rearward movement of the second detection member 18 is detected by a second detector switch 41 (see FIG. 11) provided to the pharmaceutical syringe attachment component 7, it is detected that the needle case 17 has been attached to the pharmaceutical syringe unit 10. The second detector switch 41 is disposed on the rear side of the second detection member 18 in a state in which the pharmaceutical syringe unit 10 has been attached to the pharmaceutical syringe attachment component 7.

1-4. Control Blocks

The electrical connections will now be described through reference to FIG. 25.

Figure 25:
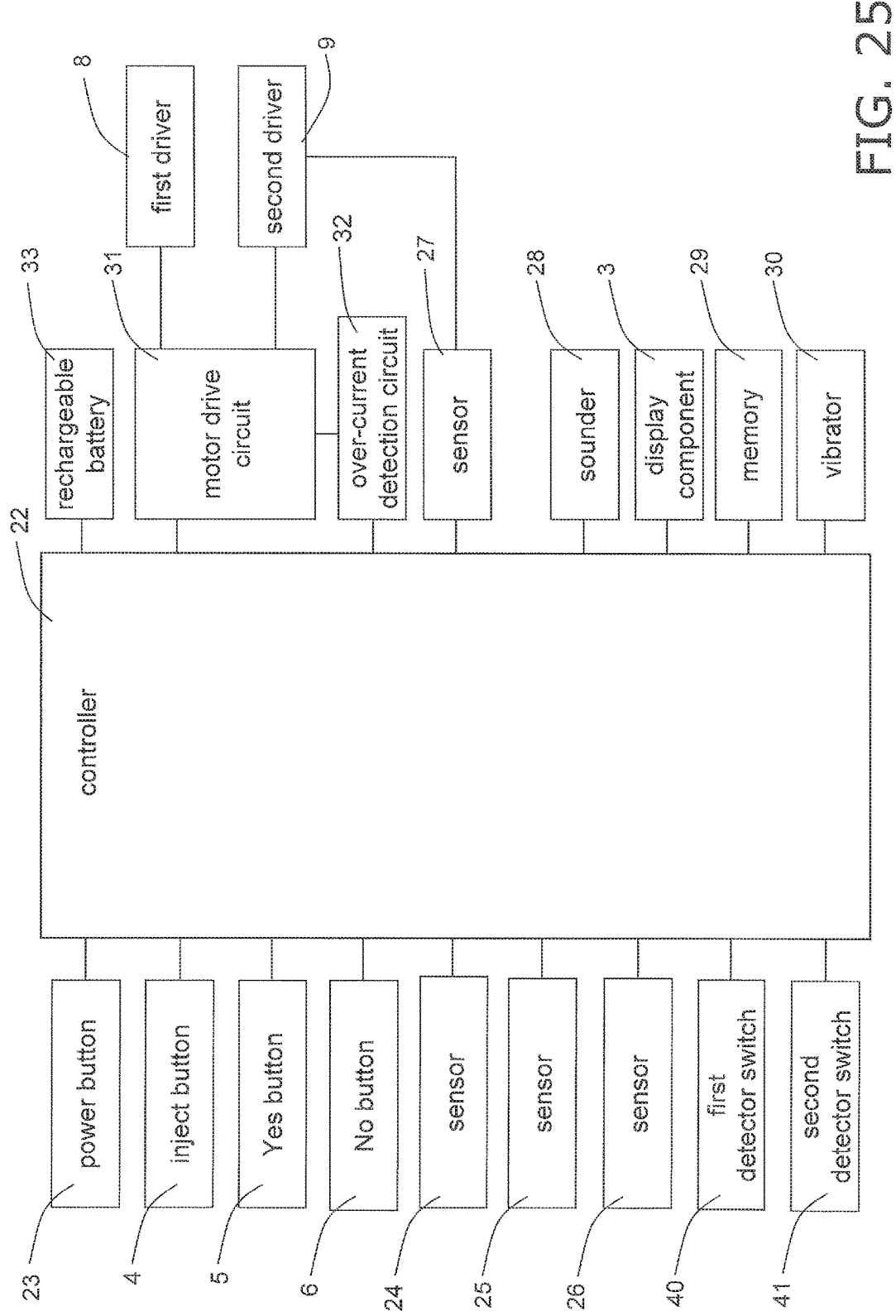
FIG. 25 is an electrical circuit block diagram of the pharmaceutical injection device pertaining to an embodiment of the present invention.

The display component 3, the inject button 4, the Yes button 5, the No button 6, the first driver 8, and the second driver 9 are connected to a controller 22 as shown in FIG. 25.

This controller 22 is also connected to the power button 23, sensors 24, 25, 26, and 27, a sounder 28, a memory 29, a vibrator 30, a motor drive circuit 31, an over-current detection circuit 32, a rechargeable battery 33, the first detector switch 40, and the second detector switch 41.

Figure 9:
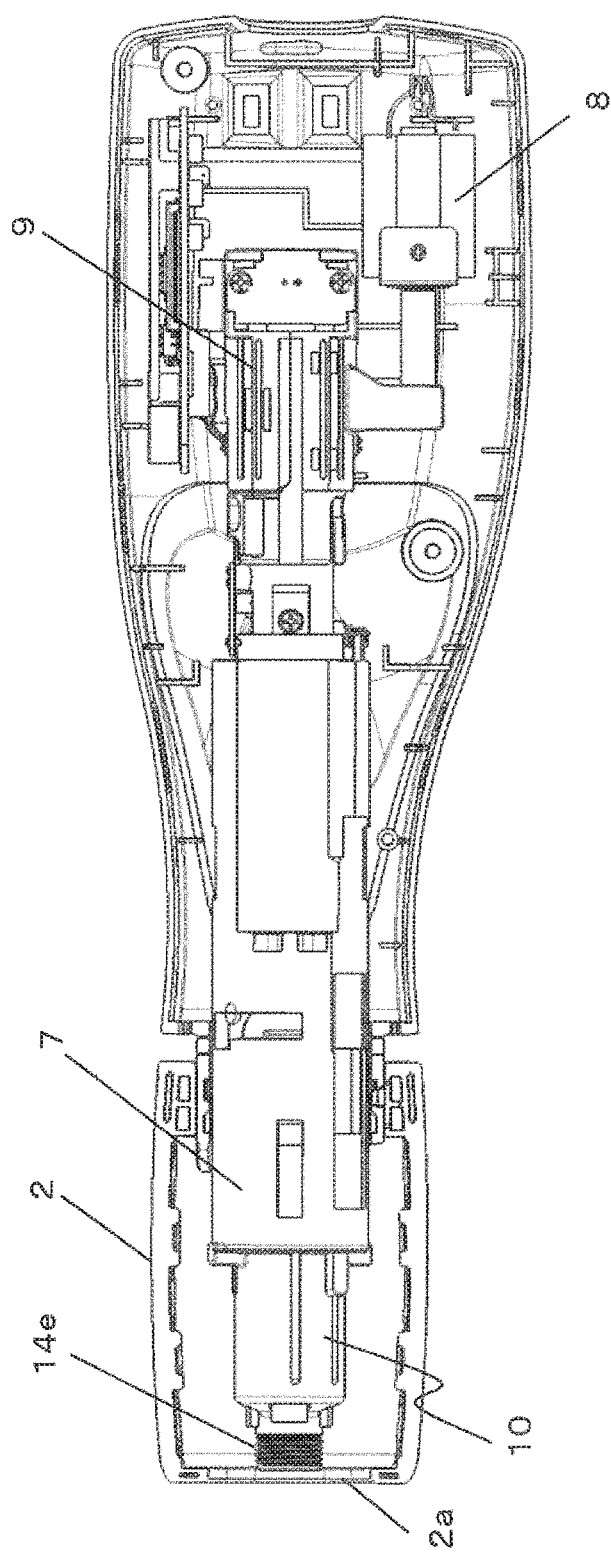
FIG. 9 is a front view of the internal configuration of the pharmaceutical injection device pertaining to an embodiment of the present invention (with front cover removed; needle replacement position)
Figure 10:
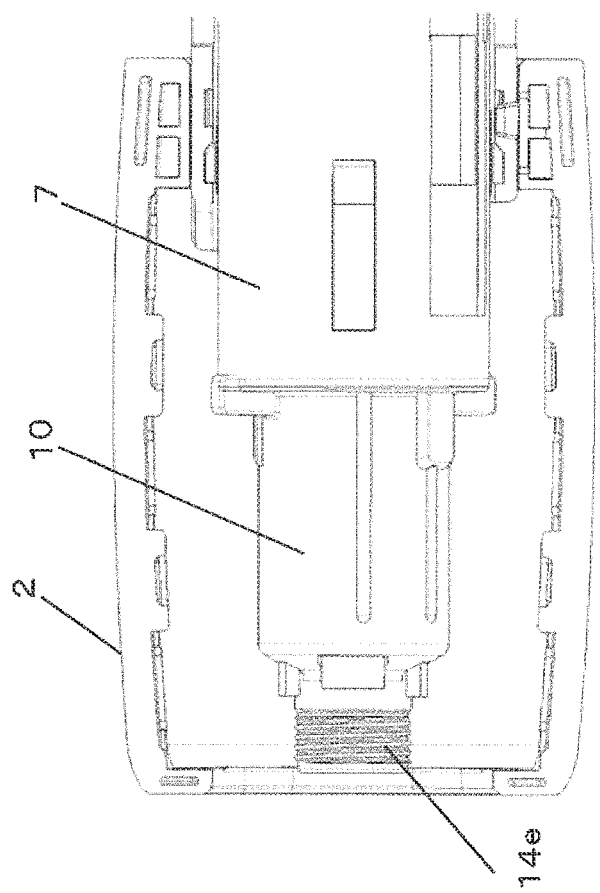
FIG. 10 is a detail configuration view of the main components in FIG. 9.

As shown in FIG. 3, the sensor 24 is used to detect that the pharmaceutical syringe unit 10 and the pharmaceutical syringe attachment component 7 (including the inner case 12) have been moved by the first driver 8 and reached the needle replacement position shown in FIGS. 9 and 10.

Figure 21:
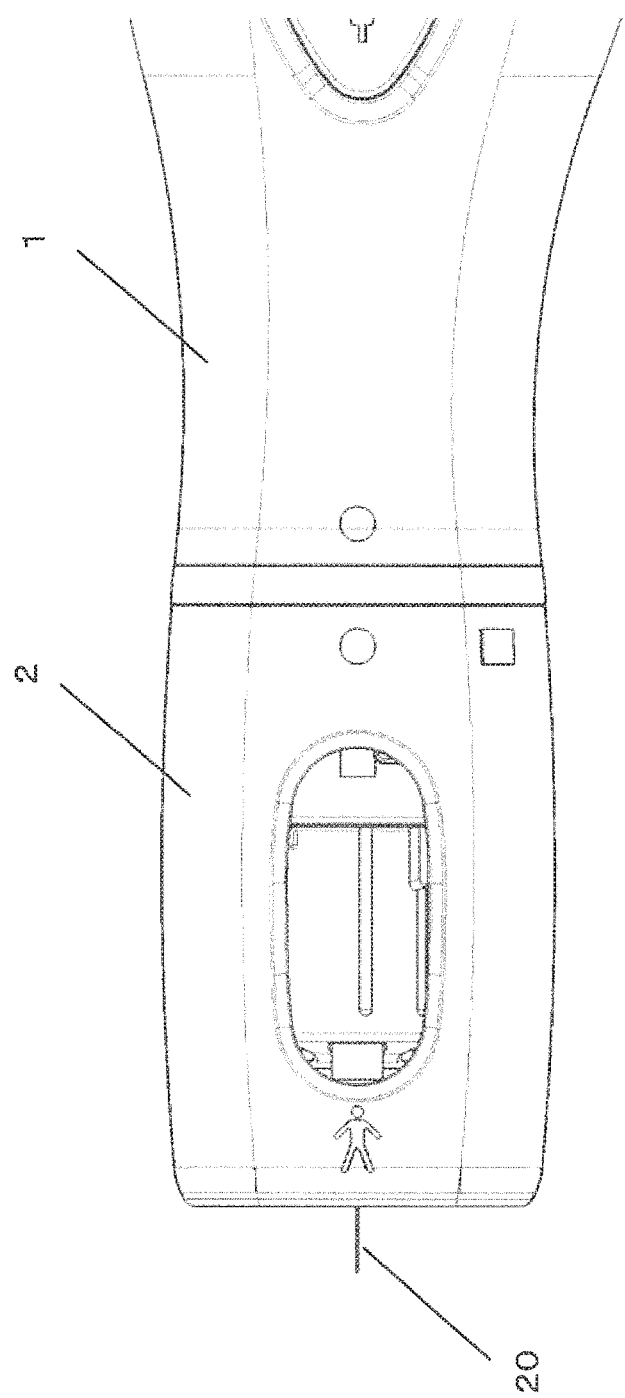
FIG. 21 is a front view of the main components of the needle insertion position of the pharmaceutical injection device when the needle case and needle cap have been removed (needle insertion position)

As shown in FIG. 3, the sensor 25 is used to detect that the pharmaceutical syringe unit 10 and the pharmaceutical syringe attachment component 7 (including the inner case 12) have been moved by the first driver 8 and reached the needle insertion position shown in FIG. 21. FIG. 21 is a front view of the main components of the distal end portion of the pharmaceutical injection device when the needle case 17 and needle cap 21 have been removed at the needle insertion position.

Figure 19:
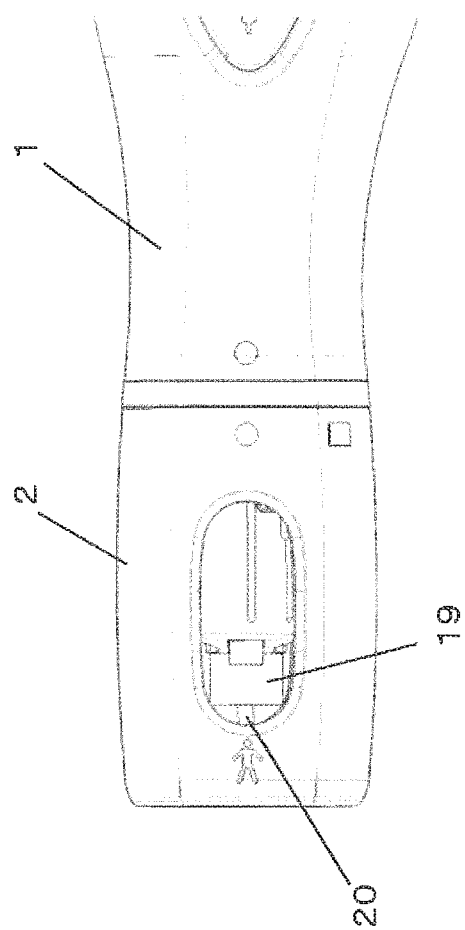
FIG. 19 is a front view of the main components at the distal end portion of the pharmaceutical injection device when a needle case and a needle cap have been removed (just prior to injection) (needle removal position)
Figure 20:
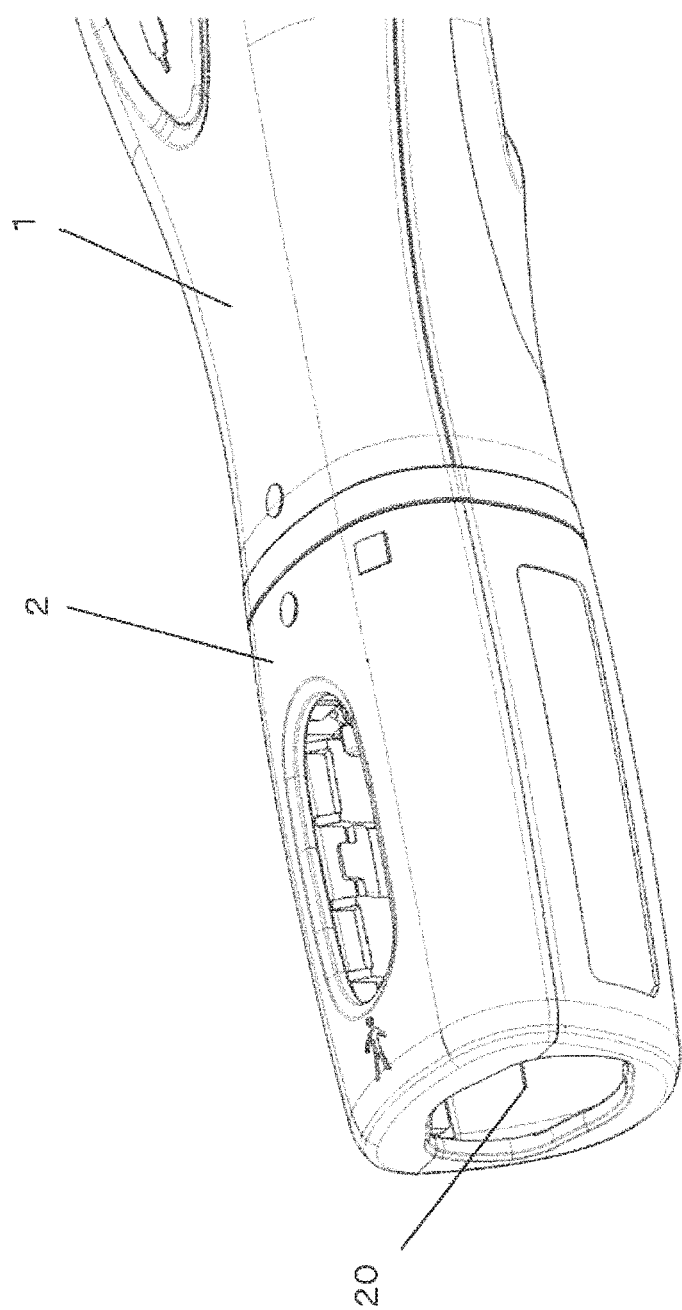
FIG. 20 is an oblique view of the main components in FIG. 19.

As shown in FIG. 3, the sensor 26 is used to detect that the pharmaceutical syringe unit 10 and the pharmaceutical syringe attachment component 7 (including the inner case 12) have been moved by the first driver 8 and reached the needle removal position (also called the home position) shown in FIGS. 19 and 20. FIG. 19 is a front view of the main components at the distal end portion of the pharmaceutical injection device when the needle case 17 and the needle cap 21 have been removed in the needle removal position (the state just prior to injection).

These sensors 24, 25, and 26 can be photosensors or the like, and they detect the position where light is blocked by the a protrusion 100 (see FIG. 3) provided to the housing in which the second driver 9 is disposed.

Since the sensors 24, 25, and 26 are disposed in that order from the distal end side toward the rear side, the needle replacement position, the needle insertion position, and the needle removal position are provided in the order from the distal end side toward the rear side.

The "needle insertion position" here is the position where the pharmaceutical is injected into a human body (an example of a subject). More specifically, as shown in FIG. 21, it is a position at which the injection needle 20 is located closer to the distal end side than the distal end cap 2.

Figure 18:
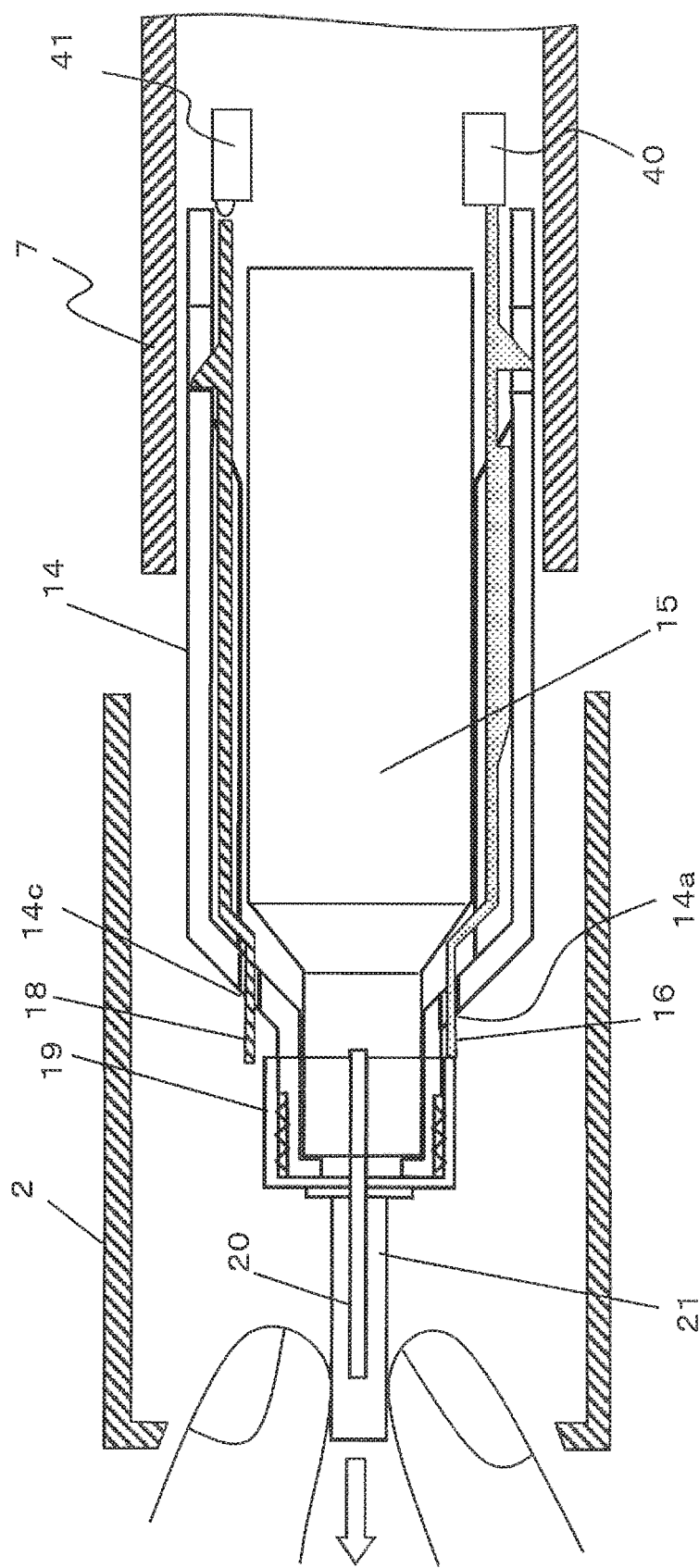
FIG. 18 is a detail cross section of the main components around the distal end cap in FIG. 16.

The "needle removal position" is the position at which the needle case 17 and the needle cap 21 are removed from the pharmaceutical syringe unit 10 to expose the injection needle 20, and is the position for covering the needle case 17 to the injection needle 20 after the injection of the pharmaceutical. More specifically, as shown in FIG. 18, it is a position at which the injection needle 20 is disposed inside the distal end cap 2 and does not protrude from the distal end cap 2.

The "needle replacement position" (an example of a needle operation position) is the position at which the attachment and removal of the needle unit 13 are performed, and is a position closer to the distal end side than the needle removal position. More specifically, as shown in FIG. 12, for example, the needle replacement position is the position at which the knurled part 17c of the needle case 17 (discussed below) is located closer to the distal end side than the distal end cap 2. Also, as shown in FIG. 11, the distance d1 from the end face 2b of the distal end cap 2 to the end face 14f of the syringe cover 14 is set to approximately 1.6 mm, for example.

The sensor 27 (see FIG. 3) senses the amount of movement of the gasket 34 (see FIG. 4). Specifically, the second driver 9 moves the piston 11 to the distal end side, and the sensor 27 senses how much the gasket 34 (see FIG. 4) which is provided at the rear end part of the pharmaceutical syringe 15 has been moved. An encoder is an example of the sensor 27.

Figure 15:
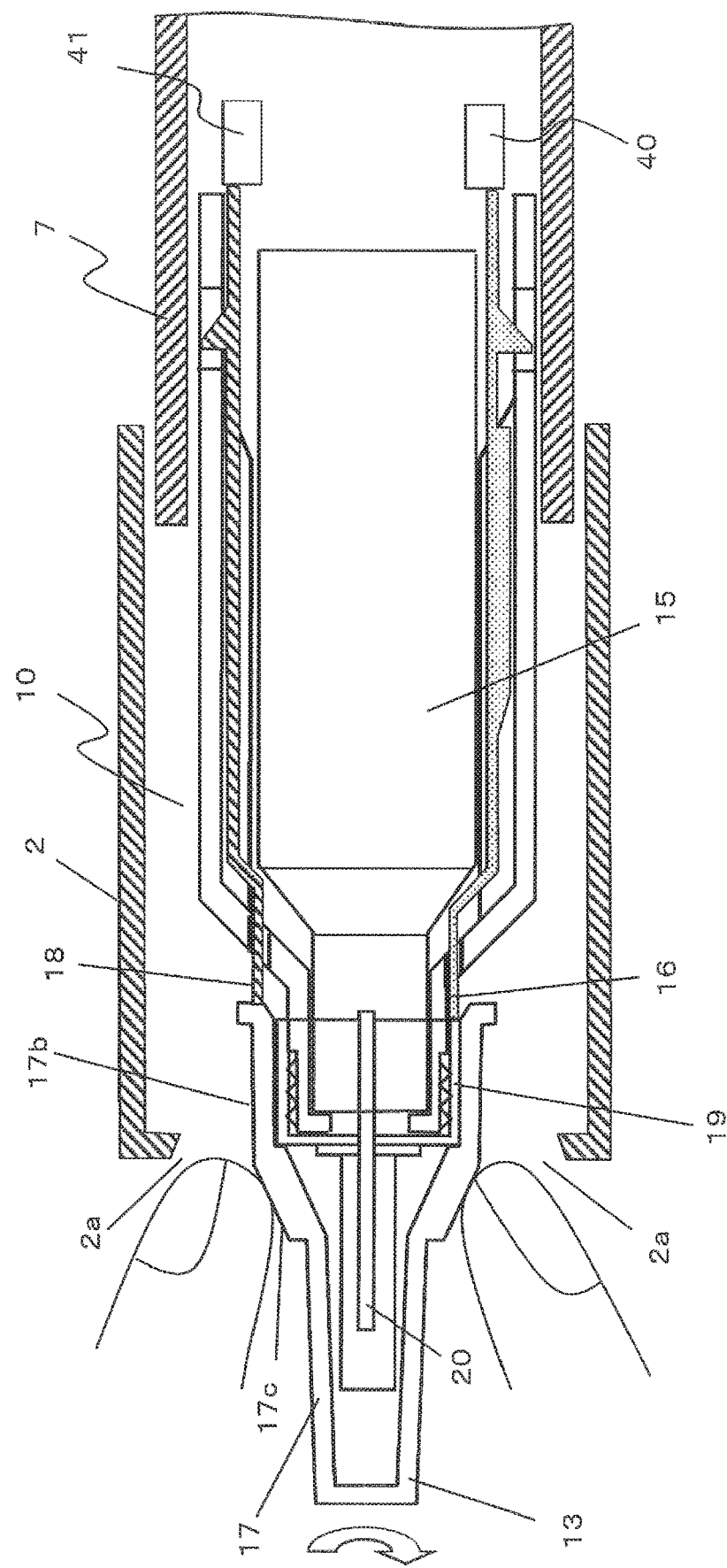
FIG. 15 is a detail cross section of the main components when the needle unit has been attached.

FIG. 15 shows the state when the needle unit 13 has been attached to the pharmaceutical syringe unit 10.

Figure 11:
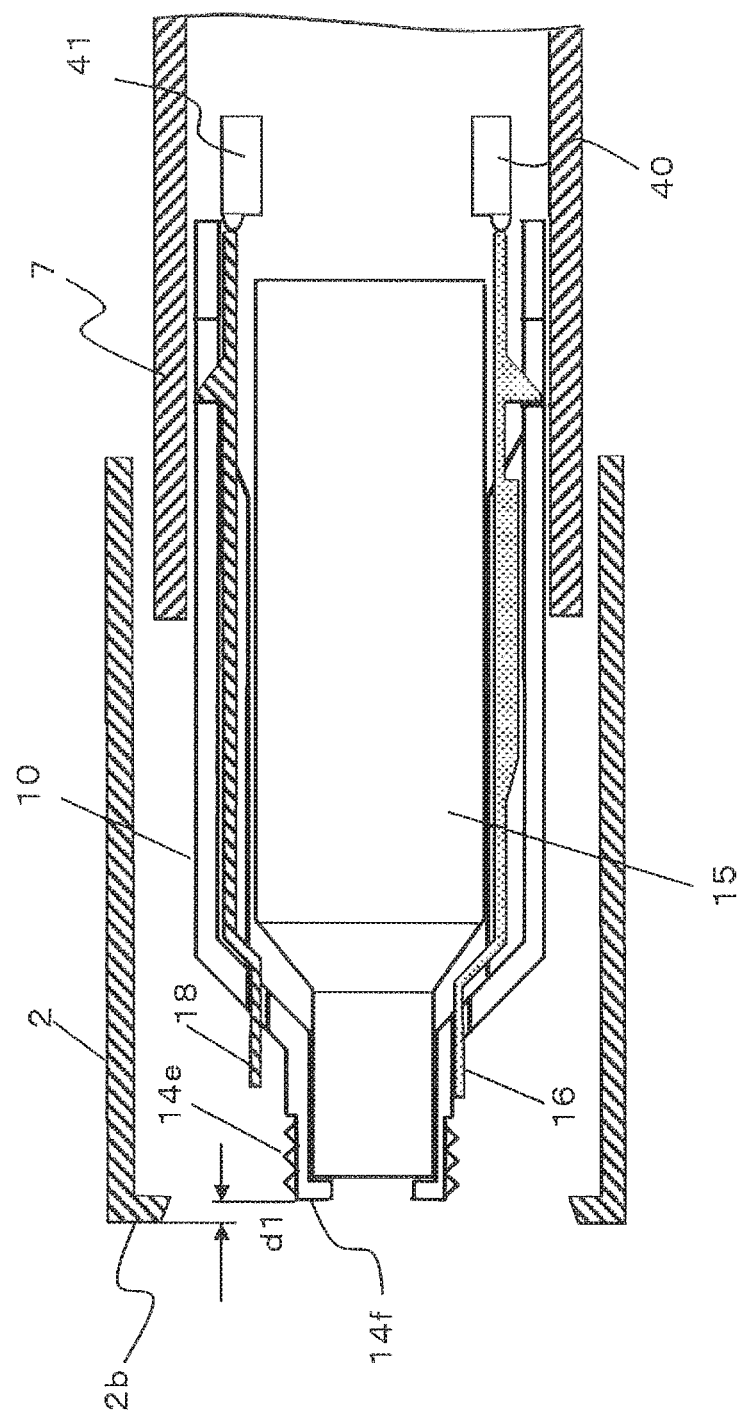
FIG. 11 is a detail cross section of the main components in FIG. 9.
Figure 12:
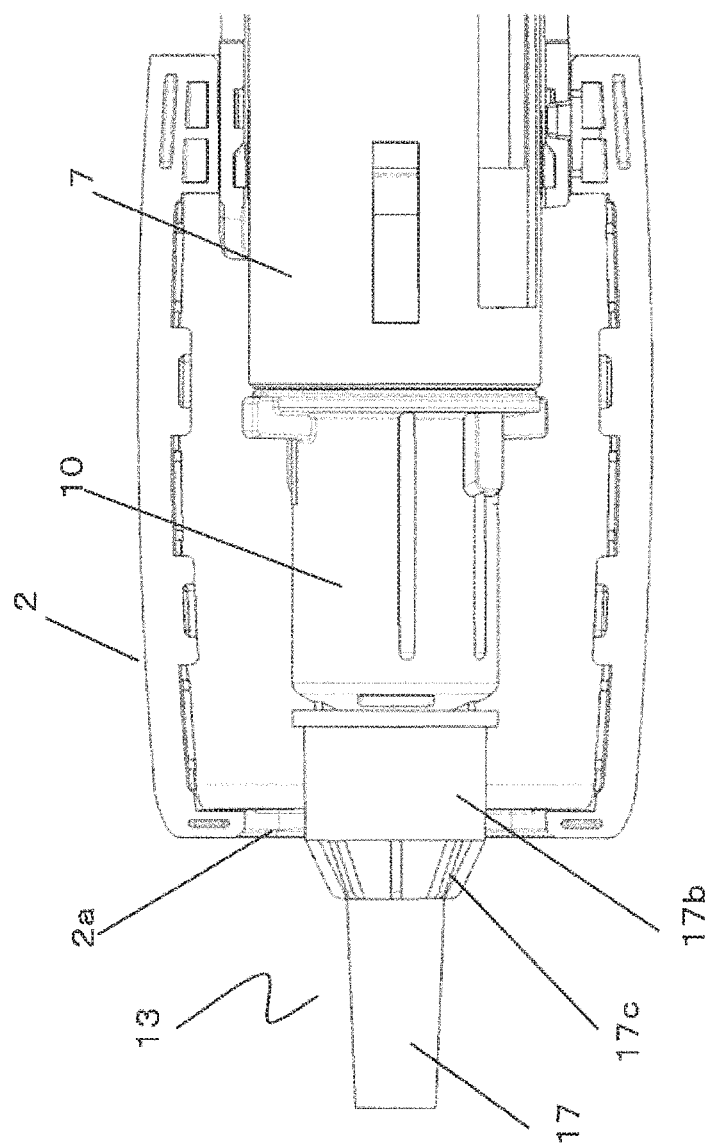
FIG. 12 is a detail configuration view of the main components when a needle unit has been attached in FIG. 10.

As shown in FIGS. 11 and 15, when the injection needle 20 is attached to the pharmaceutical syringe unit 10 in a state in which the pharmaceutical syringe unit 10 has been attached to the pharmaceutical syringe attachment component 7, the first detection member 16 moves rearward, and the first detector switch 40 is switched on, so the controller 22 can conclude that the injection needle 20 has been attached.

Meanwhile, when the injection needle 20 is removed from the pharmaceutical syringe unit 10 in a state in which the pharmaceutical syringe unit 10 has been attached to the pharmaceutical syringe attachment component 7, the first detection member 16 is moved to the distal end side by a biasing member (not shown). Therefore, the first detector switch 40 is switched off, and the controller 22 can conclude that the injection needle 20 has been removed.

If the needle case 17 is attached to the pharmaceutical syringe unit 10 in a state in which the pharmaceutical syringe unit 10 has been attached to the pharmaceutical syringe attachment component 7, the second detection member 18 moves rearward, and the second detector switch 41 is switched on, so the controller 22 can conclude that the needle case 17 has been attached.

On the other hand, if the needle case 17 is removed from the pharmaceutical syringe unit 10 in a state in which the pharmaceutical syringe unit 10 has been attached to the pharmaceutical syringe attachment component 7, the second detection member 18 is moved to the distal end side by a biasing member (not shown). Therefore, the second detector switch 41 is switched off, and the controller 22 can conclude that the needle case 17 has been removed.

The first driver 8 and the second driver 9 are driven by the motor drive circuit 31, and any over-current during this drive is detected by the over-current detection circuit 32.

The sounder 28 emits sound, such as a warning, while the vibrator 30 emits warnings and so forth with vibration.

The memory 29 holds programs for controlling the injection operation shown in FIGS. 26 to 29, for example.

2. Operation

With the above configuration, the pharmaceutical injection device in this embodiment is as shown in FIGS. 1 and 2 in its initial state. FIGS. 1 and 2 show a state in which the distal end cap 2 has been removed, the pharmaceutical syringe unit 10 has been attached to the pharmaceutical syringe attachment component 7, after which the distal end cap 2 has been attached.

That is, in the initial state, the pharmaceutical syringe unit 10 has been attached to the pharmaceutical syringe attachment component 7, at which point the threads 14e at the distal end of the syringe cover 14 are still inside the distal end cap 2 (see FIG. 2).

Figure 26:
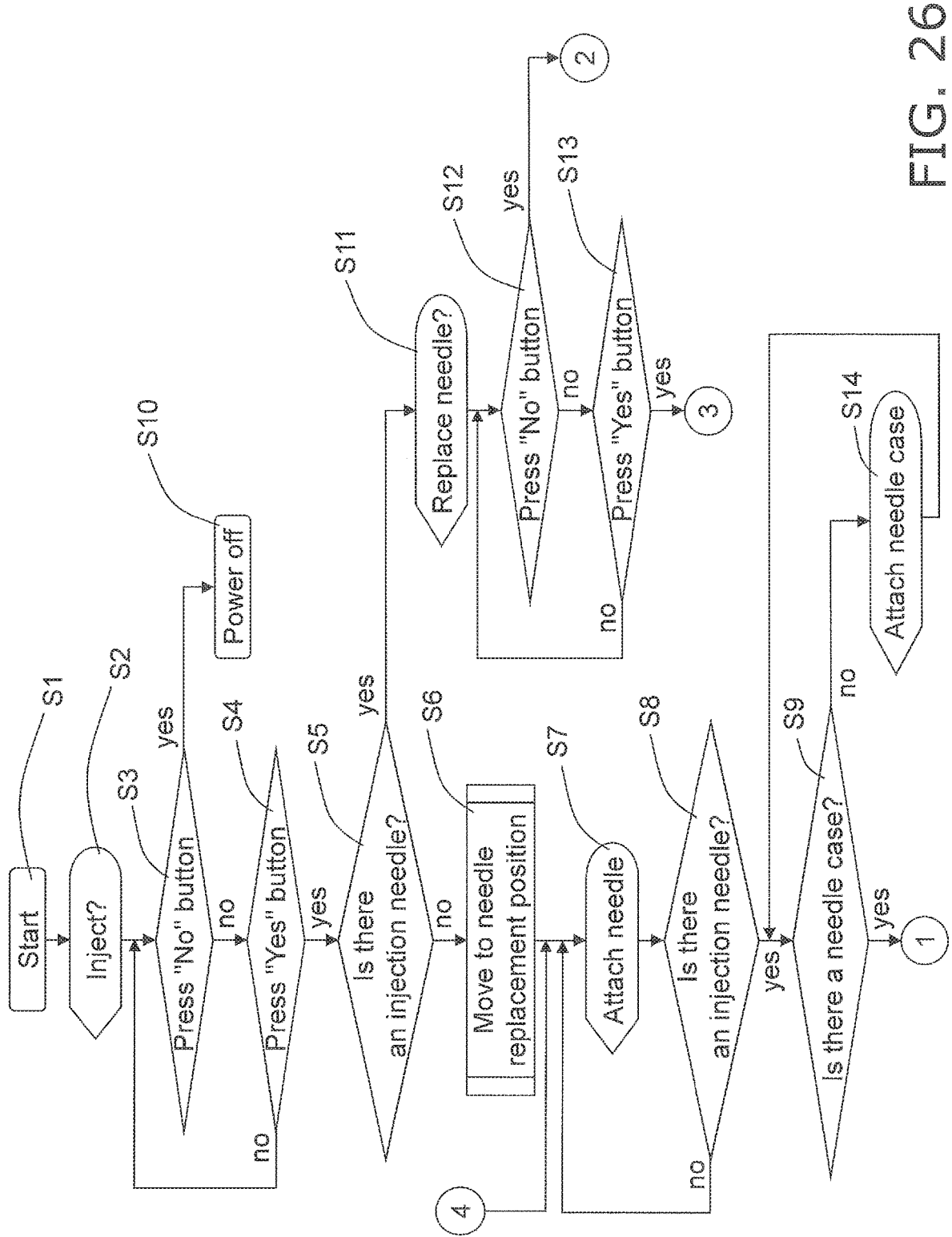
FIG. 26 is a flowchart of the pharmaceutical injection device pertaining to an embodiment of the present invention.
Figure 30:
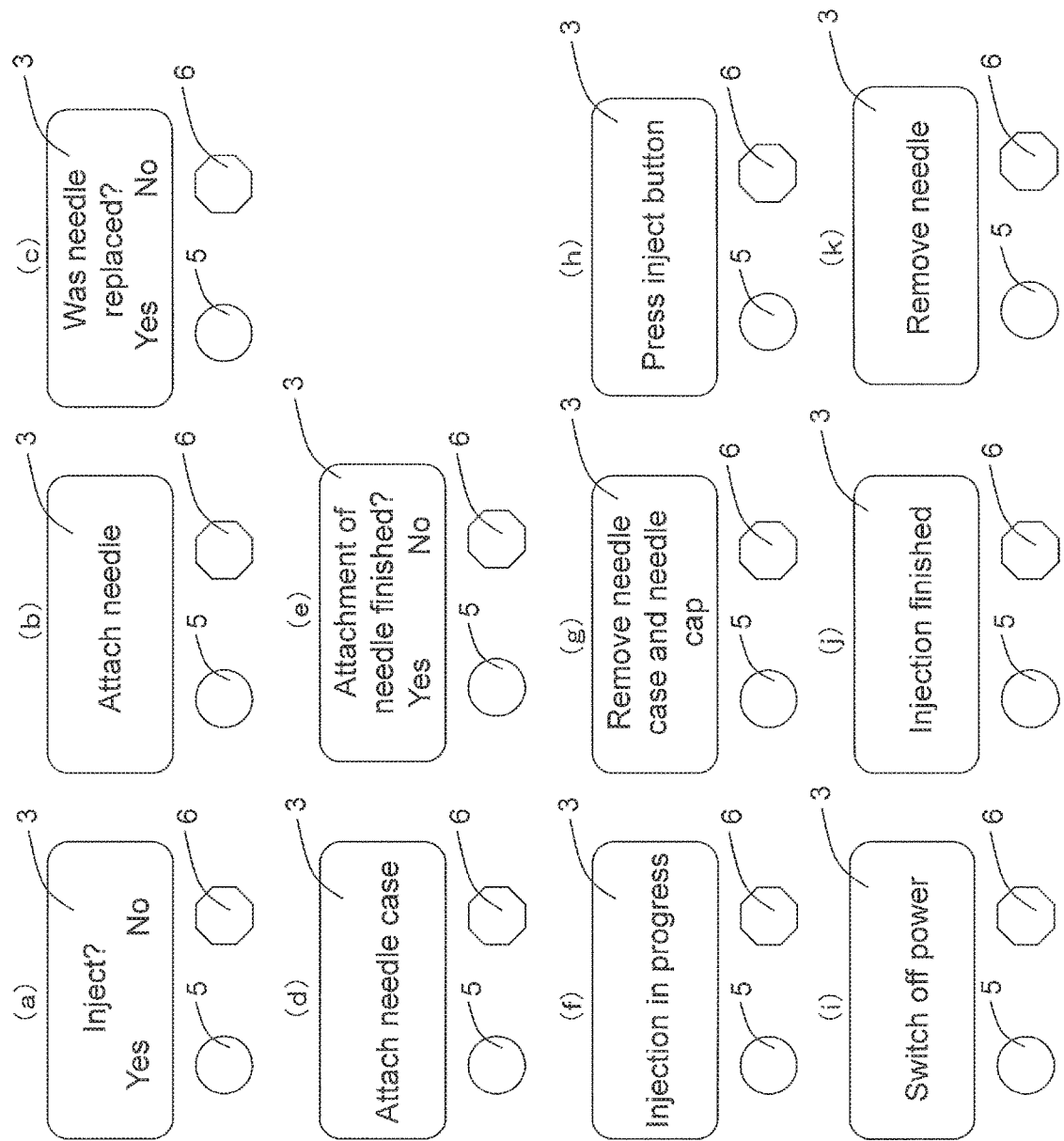
FIG. 30 is a diagram of the display of the pharmaceutical injection device pertaining to an embodiment of the present invention.

Next, to perform injection, the power button 23 is turned on (S1 in FIG. 26), and the controller 22 causes the display component 3 to display a message asking whether or not to inject, as shown in FIG. 30a (S2 in FIG. 26).

If the Yes button 5 is pressed in this state, the first detection member 16 and the first detector switch 40 shown in FIGS. 4 to 8 detect the attached state of the injection needle 20 (more precisely, the needle base 19) (S3, S4, and S5 in FIG. 26).

If the injection needle 20 has not been attached to the pharmaceutical syringe unit 10, the first driver 8 moves the pharmaceutical syringe unit 10 and the pharmaceutical syringe attachment component 7 (including the inner case 12) to the needle replacement position (S6 in FIG. 26).

At this point, the sensor 24 detects that the pharmaceutical syringe unit 10 and the pharmaceutical syringe attachment component 7 (including the inner case 12) have been moved by the first driver 8 and reached the needle replacement position shown in FIG. 9.

When this happens, the controller 22 causes the display component 3 to give a display prompting the attachment of the injection needle 20 (S7 in FIG. 26).

Upon seeing this display, the user grasps the needle case 17 of the needle unit 13 (integrated), and meshes the threads 19b provided around the inside of the needle base 19 (located inside) with the threads 14e at the distal end part of the pharmaceutical syringe unit 10 shown in FIGS. 9 and 10.

As shown in FIGS. 12, 13, and 15, a large-diameter part 17b is provided to the rear of the needle case 17, and a knurled part 17c is provided here to keep the user's fingers from slipping. This makes the needle case 17 easier to turn, and as a result the needle unit 13 can be easily attached to the distal end side of the pharmaceutical syringe unit 10.

As shown in FIGS. 12, 13, and 15, in this state the injection needle 20 protrudes to the distal end side from a distal end opening 2a in the distal end cap 2, but since the area around this is covered by the needle cap 21 and the needle case 17, inadvertent piercing of the skin can be prevented.

When the needle unit 13 is thus attached to the distal end of the pharmaceutical syringe unit 10, the first detection member 16 and the first detector switch 40 detect the attachment of the injection needle 20 (S8 in FIG. 26), and the second detection member 18 and the second detector switch 41 detect the presence or absence of the needle case 17 (S9 in FIG. 26).

Figure 27:
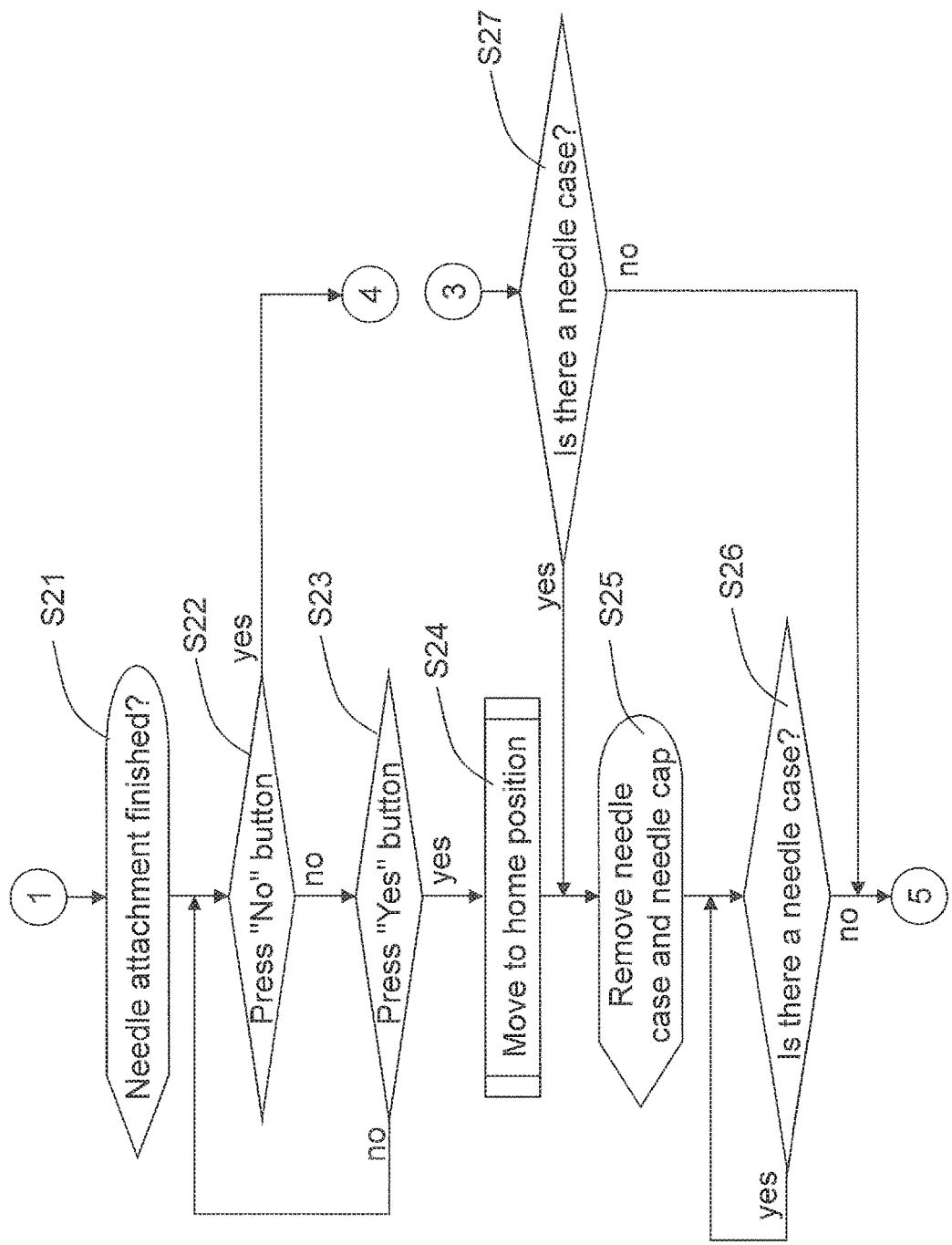
FIG. 27 is a flowchart of the pharmaceutical injection device pertaining to an embodiment of the present invention.

As shown in FIG. 30e, the controller 22 then causes the display component 3 to display a question asking whether the attachment of the injection needle 20 is complete (S21 in FIG. 27).

Figure 16:
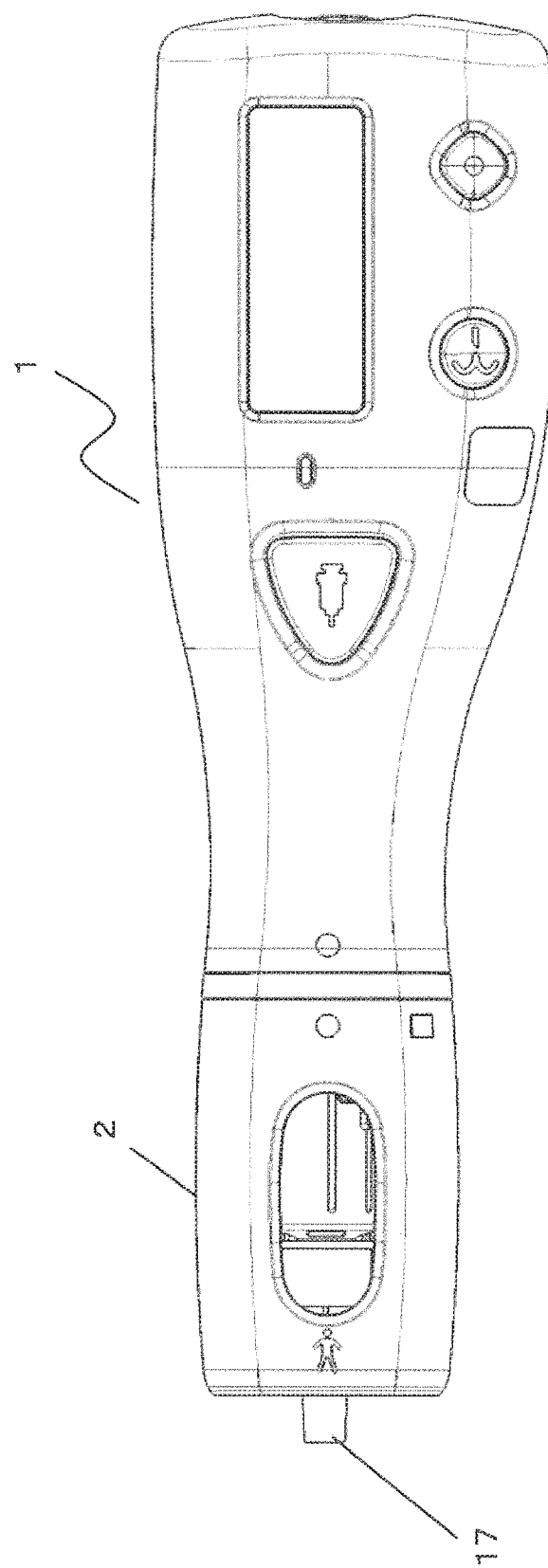
FIG. 16 is a front view of the pharmaceutical injection device when the needle unit has been attached (needle removal position)
Figure 17:
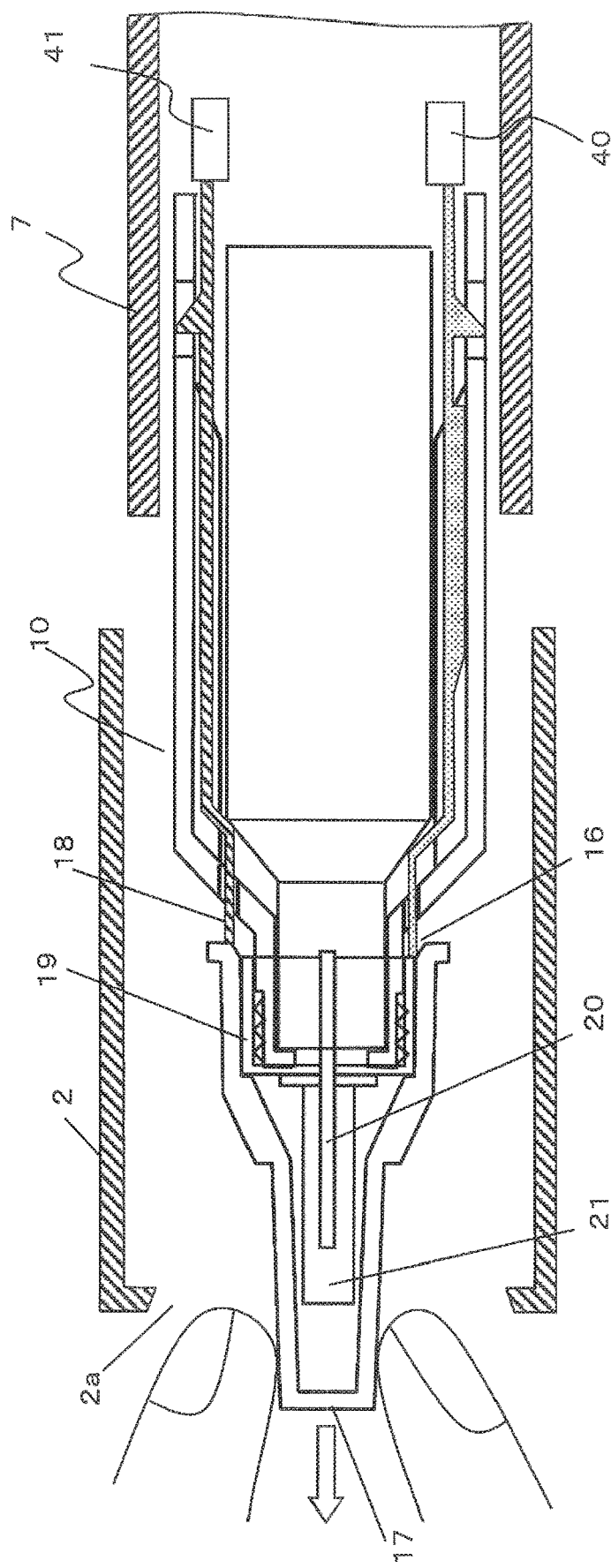
FIG. 17 is a detail cross section of the main components around the distal end cap in FIG. 16.

The user then presses the Yes button 5, and as a result, as shown in FIGS. 16 to 18, the first driver 8 moves the pharmaceutical syringe unit 10 and the pharmaceutical syringe attachment component 7 (including the inner case 12) to the needle removal position (S22, S23, and S24 in FIG. 27).

As shown in FIG. 30g, the controller 22 then causes the display component 3 to display prompting the removal of the needle case 17 and the needle cap 21 (S25 in FIG. 27). This needle removal position is the position detected by the sensor 26, as mentioned above, and is also called the needle home position.

As shown in FIGS. 16 to 18, in the state of this needle removal position, the injection needle 20 is located to the rear of the distal end opening 2a in the distal end cap 2. Therefore, as shown in FIG. 17, at the needle removal position the needle case 17 of the needle unit 13 is pulled out to the distal end side, and then as shown in FIG. 18, even if the needle cap 21 is pulled off, the injection needle 20 is still inside the distal end cap 2. This prevents inadvertent piercing of the skin.

Because the protrusions 17a of the needle case 17 and the concave parts of the bumps 19a provided to the needle base 19 are both formed extending from the distal end side to the rear side, the needle case 17 can be easily pulled out of the needle base 19.

Also, since the needle cap 21 only covers the injection needle 20 with a light engagement, it too can be easily pulled off.

As shown in FIG. 18, in a state in which the needle case 17 has been removed, the second detection member 18 moves forward, so the second detector switch 41 is off, and the controller 22 detects that the needle case 17 has been removed (S26 in FIG. 27).

Figure 28:
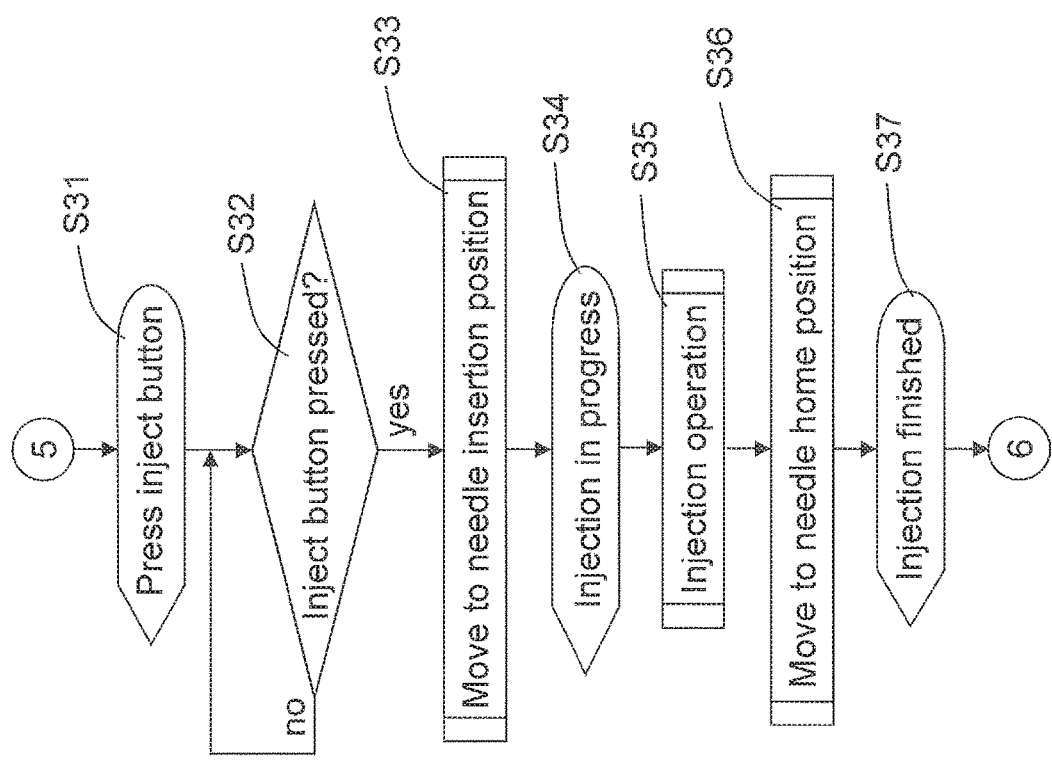
FIG. 28 is a flowchart of the pharmaceutical injection device pertaining to an embodiment of the present invention.

The controller 22 then causes the display component 3 to display telling the user to press the inject button as shown in FIG. 30h (S31 in FIG. 28).

Figure 22:
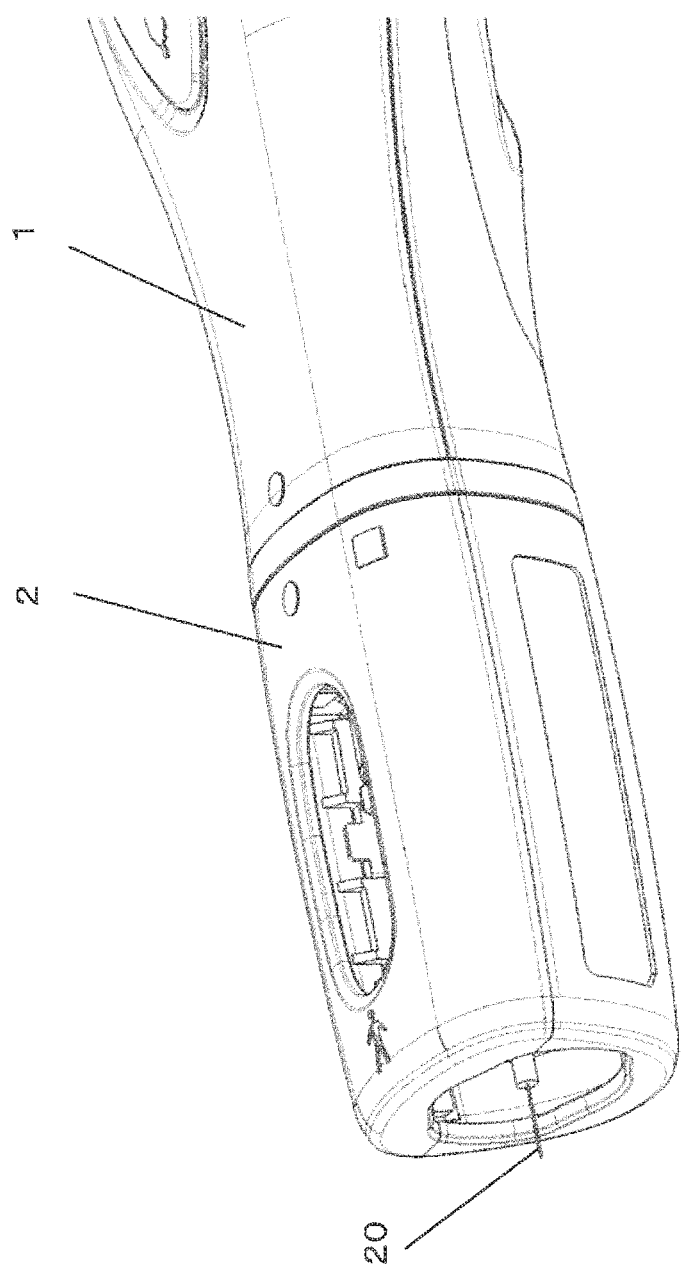
FIG. 22 is an oblique view of the main components in FIG. 21.

When the user places the distal end cap 2 against the injection position on the skin, and presses the inject button 4 in this state (S32 in FIG. 28), the first driver 8 moves the pharmaceutical syringe unit 10 and the pharmaceutical syringe attachment component 7 (including the inner case 12) to the distal end side. This movement causes the injection needle 20 to stick out from the distal end cap 2, as shown in FIGS. 21 and 22. Consequently, the needle pierces the skin (S33 in FIG. 28). After this, the display component 3 displays a message to the effect that injection is in progress (S34 in FIG. 28), as shown in FIG. 30f.

Then, the controller 22 uses the second driver 9 to move the piston 11 to the distal end side, which results in a specific amount of the pharmaceutical inside the pharmaceutical syringe 15 being injected through the injection needle 20 into the body (S35 in FIG. 28).

Once the preset specific amount has been injected as above, the piston 11 usually stops at that position. The next injection will then start from that position, but if all of the pharmaceutical in the pharmaceutical syringe 15 has been used up, for example, the piston 11 is moved rearward to its initial position (the home position of the piston 11) by the second driver 9 in order to replace the pharmaceutical syringe 15.

However, the movement to the initial position (the home position of the piston 11) is performed after movement to the needle home position.

After the injection operation is finished, the controller 22 uses the first driver 8 to move the injection needle 20 (along with the pharmaceutical syringe attachment component 7) rearward to the needle removal position (S36 in FIG. 28), and causes the display component 3 to display that the injection operation is finished, as shown in FIG. 30j (S37 in FIG. 28).

Figure 29:
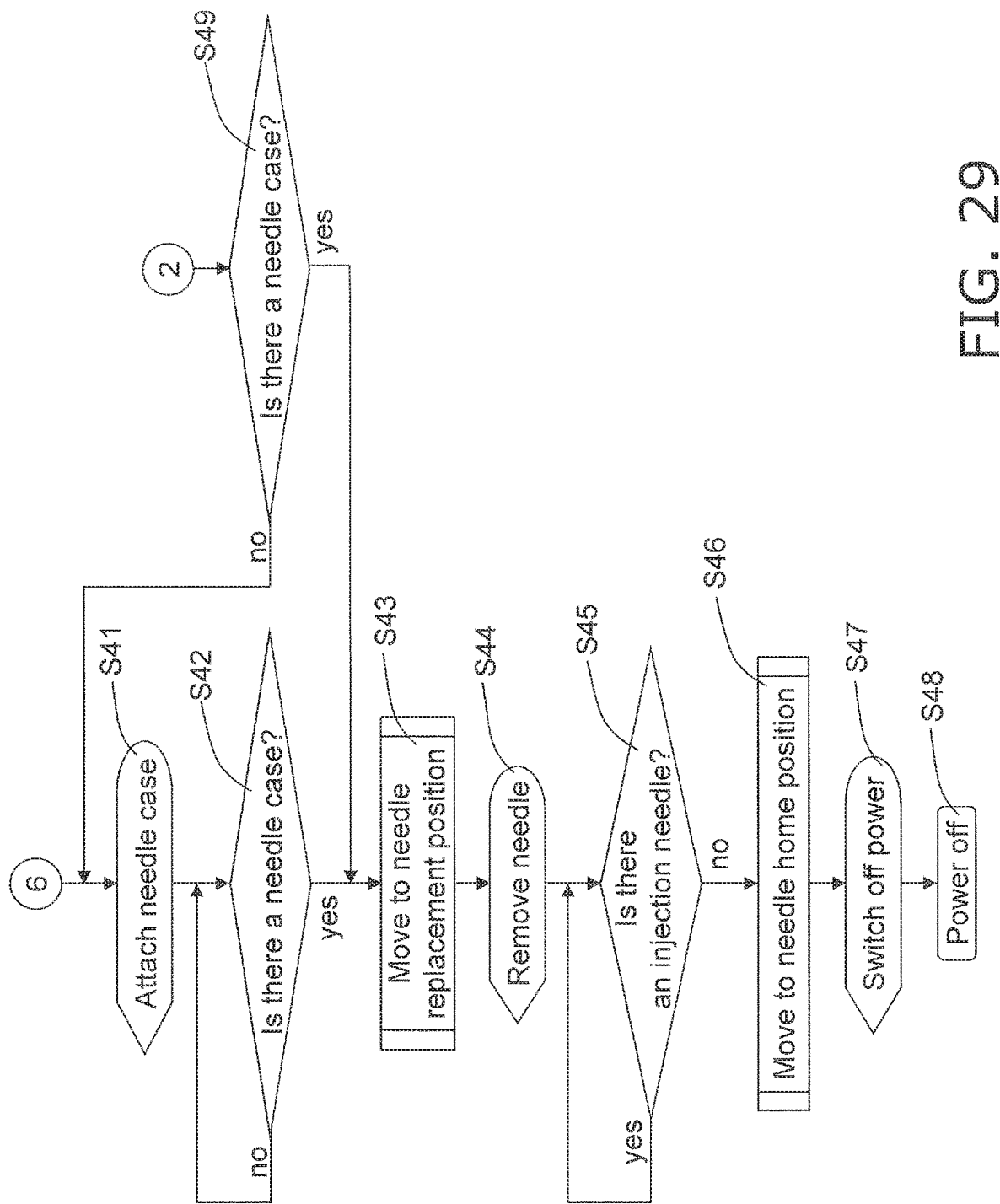
FIG. 29 is a flowchart of the pharmaceutical injection device pertaining to an embodiment of the present invention.

After this, as shown in FIG. 30d, the controller 22 causes the display component 3 to display a message prompting the user to attach the needle case 17 (S41 in FIG. 29).

Figure 23:
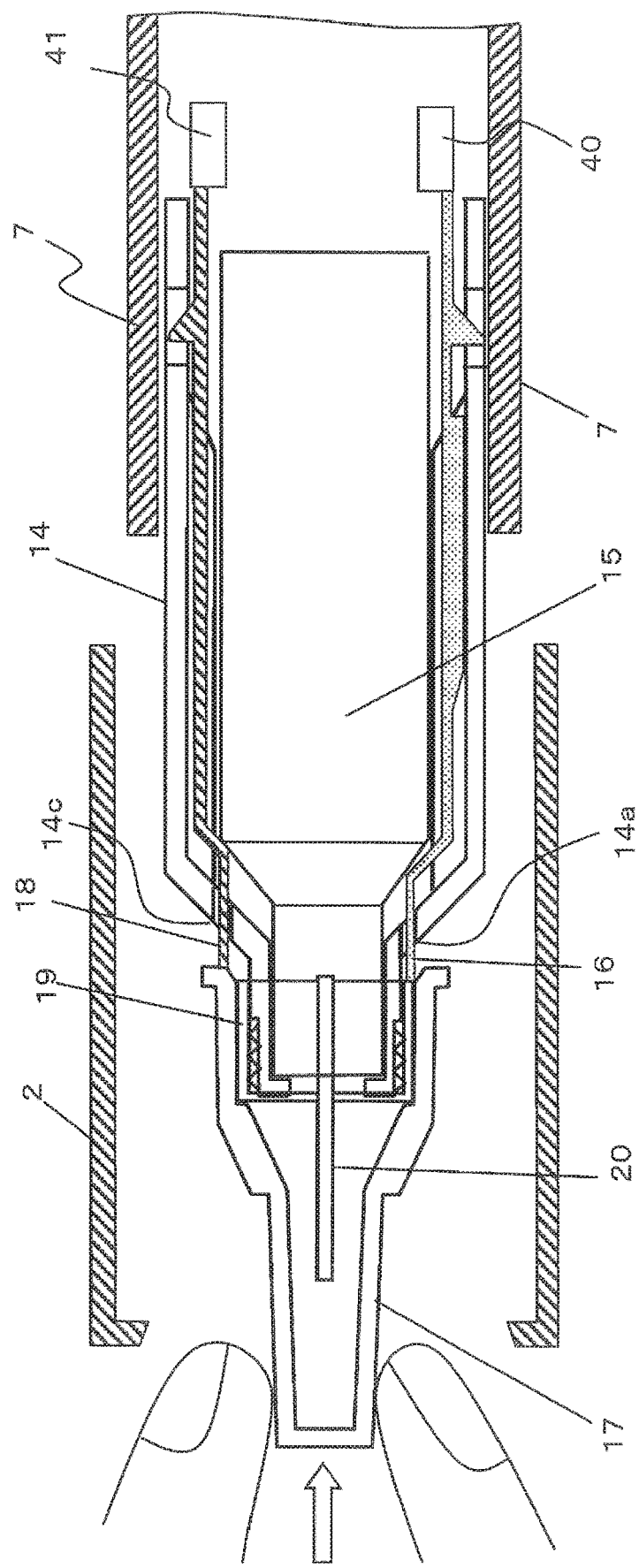
FIG. 23 is a detail cross section of the main components of the pharmaceutical injection device when the needle case has been attached after pharmaceutical injection (needle removal position)

In view of this, as shown in FIG. 23, the user inserts the needle case 17 through the distal end opening 2a in the distal end cap 2 so as to cover the outer periphery of the injection needle 20, and attaches it to the needle base 19. This completes the attachment of the needle case 17.

Figure 24:
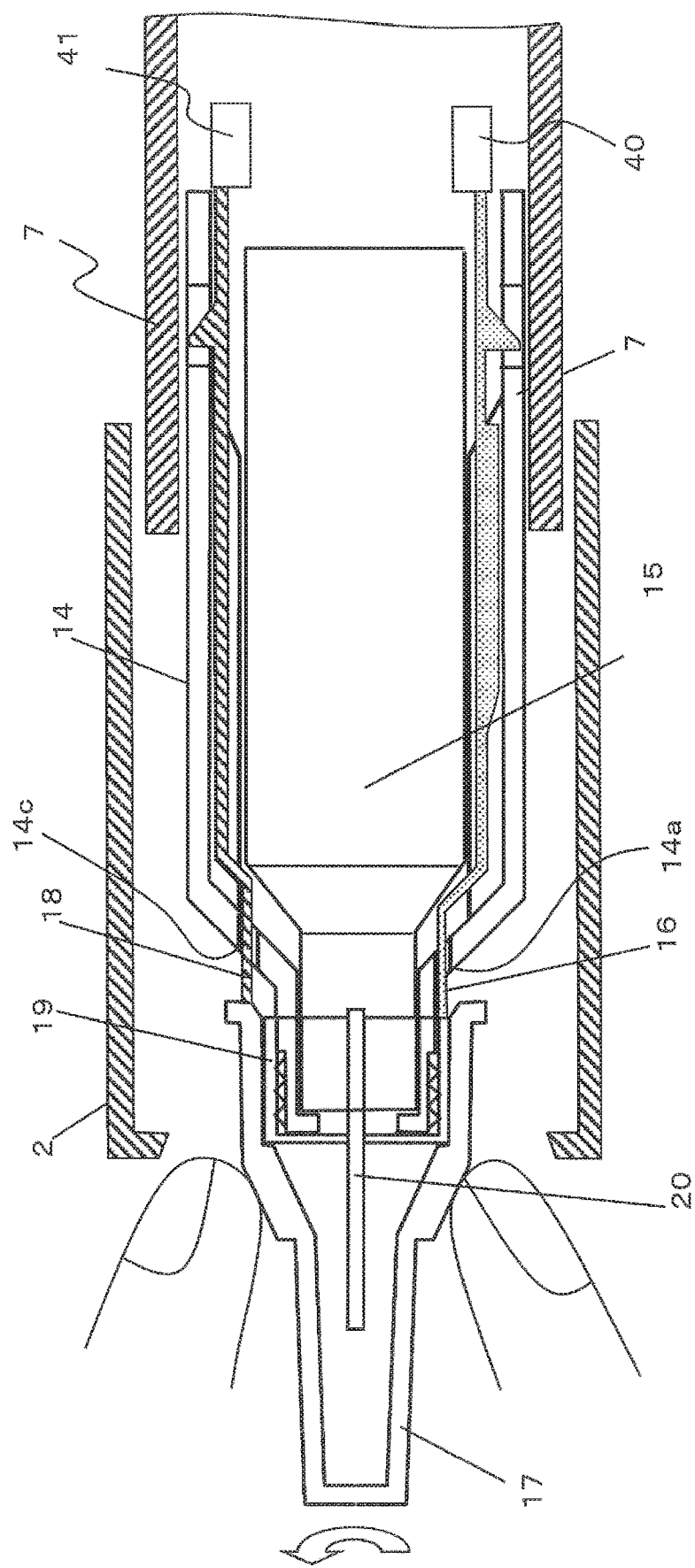
FIG. 24 is a detail cross section of the main components of the pharmaceutical injection device at the needle replacement position in FIG. 23.

When this is done, the second detection member 18 and the second detector switch 41 detect the attachment of the needle case 17 (S42 in FIG. 29), and as a result the controller 22 uses the first driver 8 to move the injection needle 20 (along with the pharmaceutical syringe attachment component 7) to the distal end side up to the needle replacement position as shown in FIG. 24 (S43 in FIG. 29). The controller 22 then causes the display component 3 to display a message prompting the user to remove the injection needle 20, as shown in FIG. 30k (S44 in FIG. 29). Here, this needle replacement position is a position that is provided closer to the distal end side than the above mentioned needle insertion position where the injection needle 20 pierces the skin.

In view of this, the user grasps the knurled part 17c (provided for anti-slip to the needle case 17) and turns the needle case 17 as in FIG. 24. This allows the injection needle 20 to be easily removed in a state of being covered by the needle case 17.

In other words, when the injection needle 20 is removed, the knurled part 17c of the needle case 17 is exposed to the outside beyond the distal end opening 2a in the distal end cap 2 in a state in which the injection needle 20 is covered by the needle case 17, so removal of the injection needle 20 can be performed simply and safely.

When this is done, the first detection member 16 and the first detector switch 40 detect that the needle unit 13 (not including the needle cap 21 here) has been removed from the pharmaceutical syringe unit 10 (S45 in FIG. 29), so the controller 22 uses the first driver 8 to move the pharmaceutical syringe unit 10 and the pharmaceutical syringe attachment component 7 (including the inner case 12) rearward to the needle removal position as shown in FIG. 1 (S46 in FIG. 29).

In this state, the controller 22 causes the display component 3 to display a message prompting the user to turn off the power as shown in FIG. 30i (S47 in FIG. 29), and the power is switched off (S48 in FIG. 29).

The above description is of a series of normal operations, but other operations shown in FIGS. 26, 27, and 29 will now be described.

First, we will describe S10 in FIG. 26. When the power button 23 is switched on in order to perform an injection (S1 in FIG. 26), the controller 22 causes the display component 3 to display a message asking whether or not to inject, as shown in FIG. 30a (S2 in FIG. 26). In this state, if the No button 6 has been pressed, the control proceeds to S10, the power is switched off, and the processing ends.

Next, we will describe S11 in FIG. 26. When the power button 23 is switched on in order to perform an injection (S1 in FIG. 26), the controller 22 causes the display component 3 to display a message asking whether or not to inject, as shown in FIG. 30a (S2 in FIG. 26). Next, if the Yes button 5 has been pressed, but the first detection member 16 and the first detector switch 40 in S5 have detected a state in which the injection needle 20 is attached, the control proceeds to S11, and the display shown in S11 is given. That is, a message prompting needle replacement is displayed on the display component 3 as shown in FIG. 30c.

When the No button 6 is pressed (S12 in FIG. 26), control moves to S49 in FIG. 29. In S49 in FIG. 29, the second detection member 18 and the second detector switch 41 detect whether or not the needle case 17 has been attached. That is, when the needle case 17 cannot be detected, control proceeds to S41 in FIG. 29, and when the needle case 17 is detected, control moves to S43 in FIG. 29. Thus, when the power button 23 has been switched on, the injection needle 20 has already been attached, and the injection needle is not being replaced with a new one, the injection needle 20 is removed without injection being performed, and control proceeds to switch off the power.

Going back to FIG. 26, when the Yes button 5 is pressed in the state of S11 (S13 in FIG. 26), control moves to S27 in FIG. 27.

When the presence or absence of the needle case 17 is detected and the needle case 17 has been attached, control moves to S25 in FIG. 27, and when the needle case 17 is not detected, control moves to S31 in FIG. 28. Specifically, since the injection needle 20 has been replaced previously, if the needle case 17 is attached, it is removed, and if the needle case 17 is not attached, the pharmaceutical injection operation is performed in that state.

Returning to FIG. 26, in S9 in FIG. 26 if the needle case 17 is not detected, the controller 22 causes the display component 3 to display a message prompting the user to attach the needle case (S14 in FIG. 26).

Main Features

The pharmaceutical injection device in this embodiment comprises the main body case 1, the distal end cap 2, the first driver 8, the second driver 9, and the controller 22. The main body case 1 has the pharmaceutical syringe attachment component 7 on its distal end side. The distal end cap 2 is removably attached to the distal end side of the main body case 1. The first driver 8 moves the pharmaceutical syringe unit 10 attached to the pharmaceutical syringe attachment component 7 to the distal end side or the rear side. The second driver 9 moves the gasket 34 of the pharmaceutical syringe 15 constituting the pharmaceutical syringe unit 10 to the distal end side. The controller 22 is connected to the first driver 8 and the second driver 9, and uses the first driver 8 to move the pharmaceutical syringe attachment component 7 to the needle replacement position (an example of a needle operation position) that is closer to the distal end side than the needle removal position, when the injection needle 20 is attached to the pharmaceutical syringe unit 10, or when the injection needle 20 is removed from the pharmaceutical syringe unit 10.

As discussed above, in this embodiment, the controller 22 uses the first driver 8 to move the pharmaceutical syringe attachment component 7 closer to the distal end side than the needle removal position, when the injection needle 20 is attached to the pharmaceutical syringe unit 10, or when the injection needle 20 is removed from the pharmaceutical syringe unit 10. Therefore, when the injection needle 20 is attached to the pharmaceutical syringe unit 10, or when the injection needle 20 is removed from the pharmaceutical syringe unit 10, even if the distal end cap 2 is not removed from the main body case 1, the attachment or removal of the injection needle 20 can still be executed, making the device extremely convenient to use.

Other Embodiments

A

In the above embodiment, the replacement of the injection needle 20 is performed at the needle replacement position, but instead of providing a needle replacement position, needle replacement may be performed at the needle insertion position. Furthermore, this is not limited to the needle insertion position, and needle replacement may be performed in between the needle removal position and the needle insertion position. In other words, the replacement of the needle unit 13 should be carried out at a position that is closer to the distal end side than the needle removal position, but it is preferable for at least part of the knurled part 17c to stick outside from the distal end opening 2a in the distal end cap 2, because this will make it easier to replace the needle unit 13.

B

In the above embodiment, the needle cap 21 is provided to the needle unit 13, but instead of providing the needle cap 21, the configuration may be such that the needle case 17 covers the injection needle 20 directly.

Embodiment 2

Embodiment 2 of the present invention will now be described through reference to the appended drawings.

1. Configuration 1-1. Overall Summary of Pharmaceutical Injection Device

In FIGS. 31 to 33, 1001 is a main body case, and a distal end cap 1002 is removably attached to the distal end side of this main body case 1001.

A display component 1003, an inject button 1004, a Yes button 1005 for selecting "Yes" to a question, and a No button 1006 for selecting "No" to a question are provided on the front of this main body case 1001.

Figure 33:
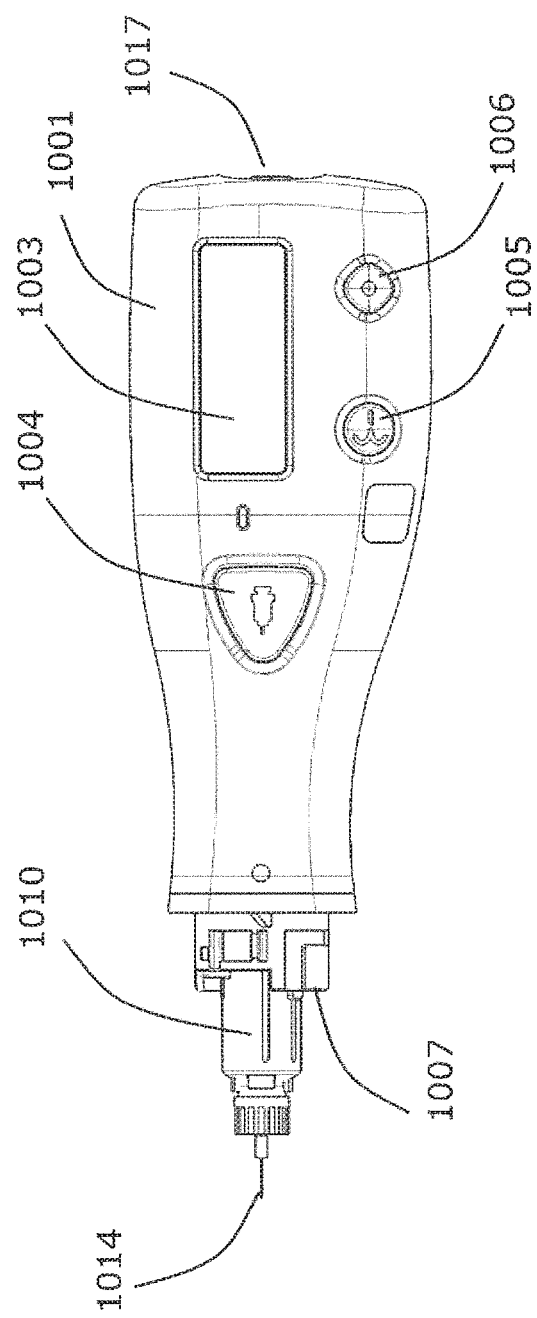
FIG. 33 is a front view of the pharmaceutical injection device in FIG. 31 (distal end cap unattached state)
Figure 34:
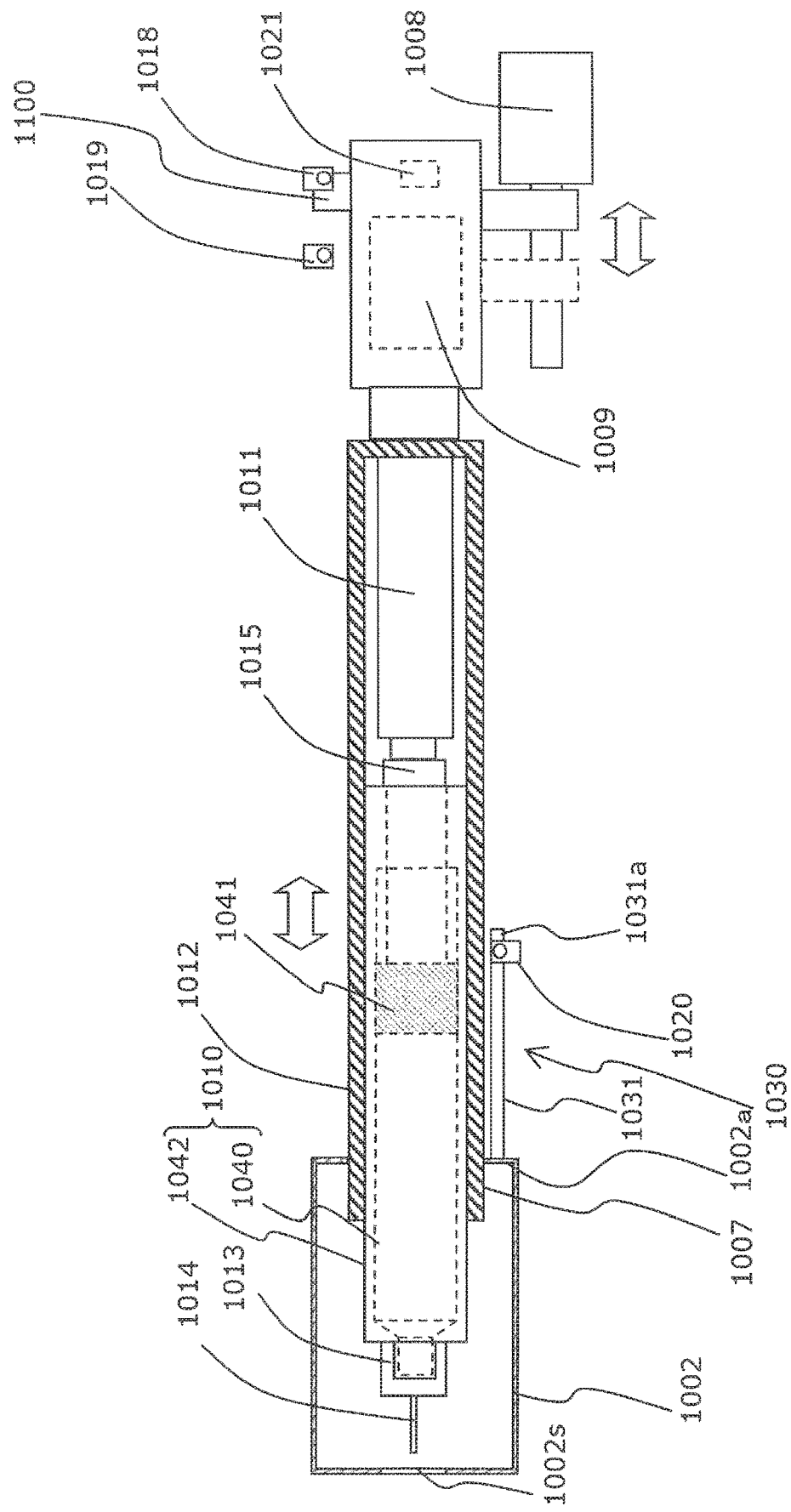
FIG. 34 is a diagram of the first and second drivers of the pharmaceutical injection device in FIG. 31.

Also, as shown in FIGS. 33 and 34, a pharmaceutical syringe attachment component 1007, a first driver 1008 that moves this pharmaceutical syringe attachment component 1007 to the distal end side or rearward from this distal end side, and a second driver 1009 that moves a piston unit 1011 to the distal end side to push out the pharmaceutical, are provided inside the main body case 1001. The first driver 1008 move the second driver 1009 to the distal end side or the rear side along with the pharmaceutical syringe attachment component 1007. The first driver 1008 and the second driver 1009 can be a stepping motor, for example.

The term "distal end side" or "front side" here refers to the distal end cap 1002 side (the side on which the injection needle is attached), and can also be called the insertion direction side of a piston 1015 into a pharmaceutical syringe 1040. Also, "rear end" or "rear side" refers to the side on which the second driver 1009 and a power button 1017 are provided, and can also be called the direction side of pulling the piston 1015 out of the pharmaceutical syringe 1040.

A pharmaceutical syringe unit 1010 is removably attached to the pharmaceutical syringe attachment component 1007.

These components will be described briefly through reference to FIG. 34.

The pharmaceutical syringe attachment component 1007 has an inner case 1012, and the pharmaceutical syringe unit 1010 is attached inside the inner case 1012. The piston unit 1011, which is driven by the second driver 1009, is disposed inside the inner case 1012 and on the rear side of the attached pharmaceutical syringe unit 1010. This piston unit 1011 has the piston 1015 that is inserted into the pharmaceutical syringe unit 1010. Also, the pharmaceutical syringe unit 1010 has a syringe case 1042 and the pharmaceutical syringe 1040 that is housed in the syringe case 1042. A gasket 1041 is provided inside this pharmaceutical syringe 1040.

The above-mentioned first driver 1008 moves the inner case 1012 constituting the pharmaceutical syringe attachment component 1007 to the distal end side or the rear side, and as a result the pharmaceutical syringe unit 1010 attached inside the inner case 1012 also moves to the distal end side or the rear side.

As shown in FIG. 34, since a needle unit 1013 is attached to the distal end part of the pharmaceutical syringe unit 1010, this needle unit 1013 also moves to the distal end side or the rear side.

This state, that is, a state in which the needle unit 1013 moves to the distal end side, is a needle insertion state. Conversely, a state in which the needle unit 1013 moves to the rear side is the needle home (needle removal) state.

The needle unit 1013 has an injection needle 1014, and during needle insertion, the injection needle 1014 protrudes to the distal end side through an opening 1002s at the distal end of the distal end cap 1002, and pierces the skin.

Also, during needle insertion, the skin is pressed against the distal end side of the distal end cap 1002, and in this state the first driver 1008 moves the injection needle 1014 to the distal end cap 1002 side along with the inner case 1012. Consequently, the injection needle 1014 pierces the skin.

After this needle insertion, the second driver 1009 drives the piston unit 1011, and the piston 1015 constituting the piston unit 1011 moves into the pharmaceutical syringe unit 1010. Consequently, the gasket 1041 of the pharmaceutical syringe 1040 constituting the pharmaceutical syringe unit 1010 moves to the distal end side, so the pharmaceutical inside the pharmaceutical syringe 1040 is injected through the injection needle 1014 into the body.

1-2. Control Blocks

The electrical connections will now be described through reference to FIG. 35.

Figure 35:
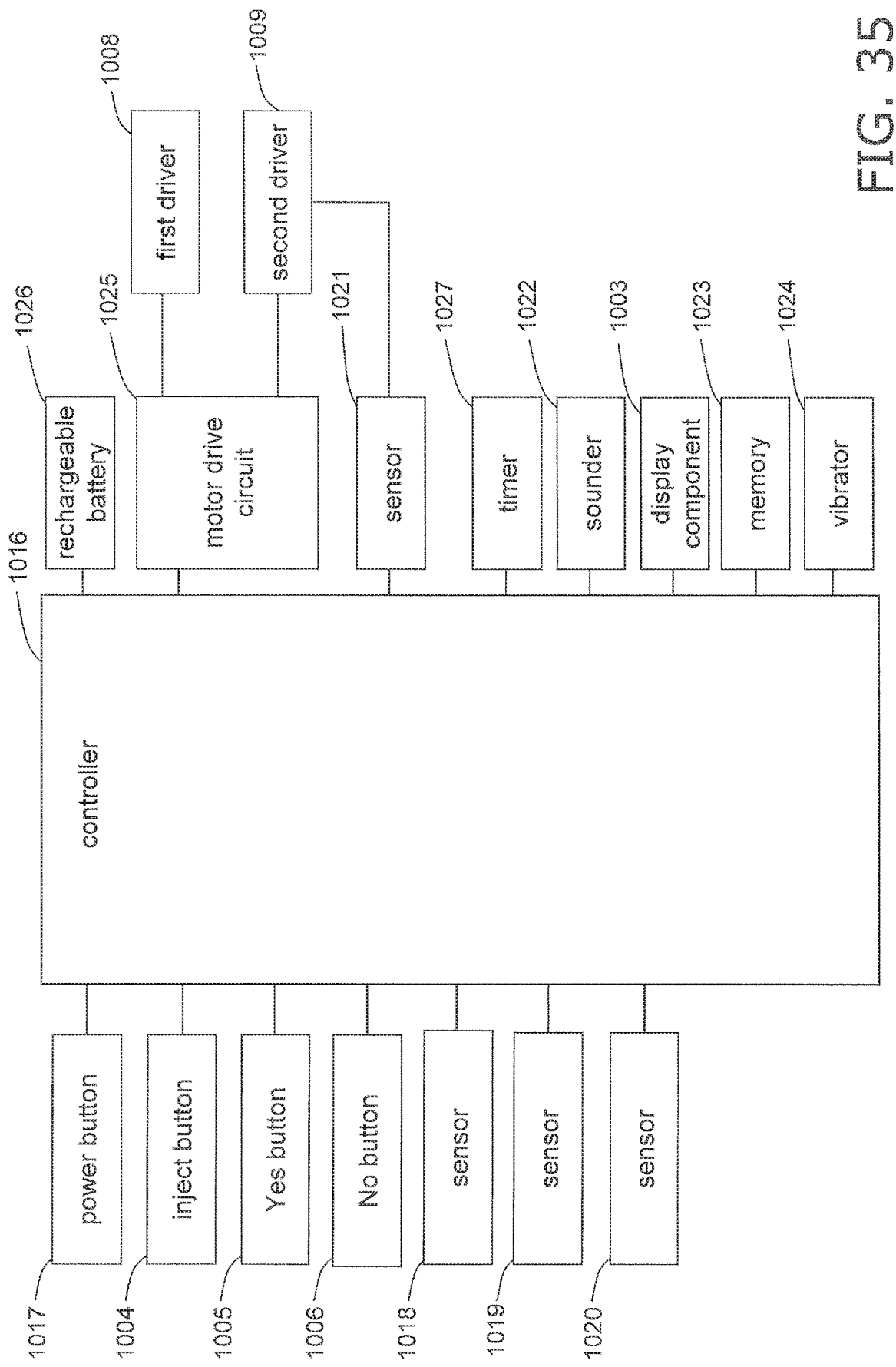
FIG. 35 is a control block diagram of the pharmaceutical injection device in FIG. 31.

The display component 1003, the inject button 1004, the Yes button 1005, the No button 1006, the first driver 1008, and the second driver 1009 are connected to a controller 1016 as shown in FIG. 35.

This controller 1016 is also connected to the power button 1017, sensors 1018, 1019, 1020, and 1021, a sounder 1022, a memory 1023, a vibrator 1024, a motor drive circuit 1025, a rechargeable battery 1026, and a timer 1027.

As shown in FIG. 34, the sensor 1018 is used to detect a state in which the pharmaceutical syringe unit 1010 and the pharmaceutical syringe attachment component 1007 (including the inner case 1012) have dropped down to the rearmost end as shown in FIG. 34. This state detected by the sensor 1018 is the state in FIG. 31, and at this point the injection needle 1014 has retracted within the distal end cap 1002.

As shown in FIG. 34, the sensor 1019 detects a state in which the pharmaceutical syringe unit 1010 and the pharmaceutical syringe attachment component 1007 (including the inner case 1012) have proceeded to the very distal end. This stated detected by the sensor 1019 is the state in FIG. 32, and at this point the injection needle 1014 sticks out to the distal end side from the distal end cap 1002, and has pierced the skin.

These sensors 1018 and 1019 can be photosensors or the like, and each have a light projector and a light receiver. A position is sensed when light is blocked by a protrusion 1100 provided to the housing in which the second driver 1009 is disposed.

Figure 32:
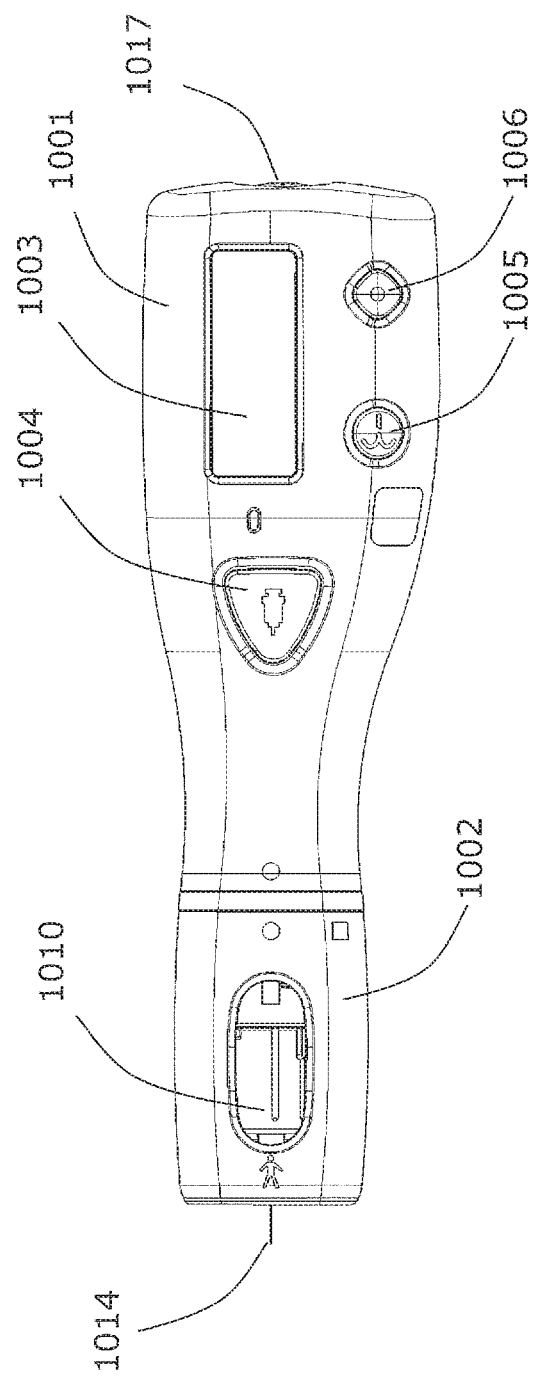
FIG. 32 is a front view of the pharmaceutical injection device in FIG. 31 (needle insertion position)

The sensor 1020 detects whether or not the distal end cap 1002 has been attached to the main body case 1001. This sensor 1020 can detect both a state in which the distal end cap 1002 has been removed from the main body case 1001 as shown in FIG. 33, and a state in which the distal end cap 1002 has been attached to the main body case 1001 as shown in FIG. 32.

The sensor 1021 senses the amount of drive of the second driver 1009. More specifically, the sensor 1021 is an encoder that senses the rotational speed of a motor constituting the second driver 1009, and is able to sense how much the piston 1015 has been pushed into the pharmaceutical syringe unit 1010.

1-3. Attached State Detector 1030

The attached state detector 1030 will now be described, which uses the above-mentioned sensor 1020 to detect the attached state of the distal end cap 1002 to the main body case 1001.

The attached state detector 1030 has a detection lever 1031, the above-mentioned sensor 1020, and a biasing member (not shown). The detection lever 1031 is supported by the main body case 1001 so as to be able to move parallel to the movement direction of the inner case 1012, and is aligned with the inner case 1012. The detection lever 1031 is biased toward the distal end side (to the left in FIG. 34) by a biasing member (not shown) (see FIG. 34). The sensor 1020 is a photosensor having a light projector and a light receiver, and the light receiver detects light from the light projector. When an obstruction is inserted between the light projector and the light receiver, the light is blocked, the light receiver can no longer detect the light, and the presence of the obstruction is detected.

When the distal end cap 1002 is attached to the main body case 1001, the rear end 1002a of the distal end cap 1002 pushes the detection lever 1031 back against the biasing force (that is, in the opposite direction from the distal end side; to the right in FIG. 34). The rear end 1031a of the detection lever 1031 then blocks the light within the sensor 1020, and the attachment of the distal end cap 1002 is detected.

That is, the output of the photosensor changes when the rear end 1031a of the detection lever 1031 goes between the above-mentioned light projector and light receiver of the sensor 1020. When the controller 1016 detects this change in the output of the photosensor, it knows that the distal end cap 1002 has been attached.

On the other hand, when the distal end cap 1002 is removed from the main body case 1001, the biasing member (not shown) moves the detection lever 1031 to the distal end side (to the left in FIG. 34), and the light within the sensor 1020 is no longer blocked by the detection lever 1031, so it is detected that the distal end cap 1002 is not attached.

2. Operation

The operation of the pharmaceutical injection device in this embodiment will now be described.

Figure 36:
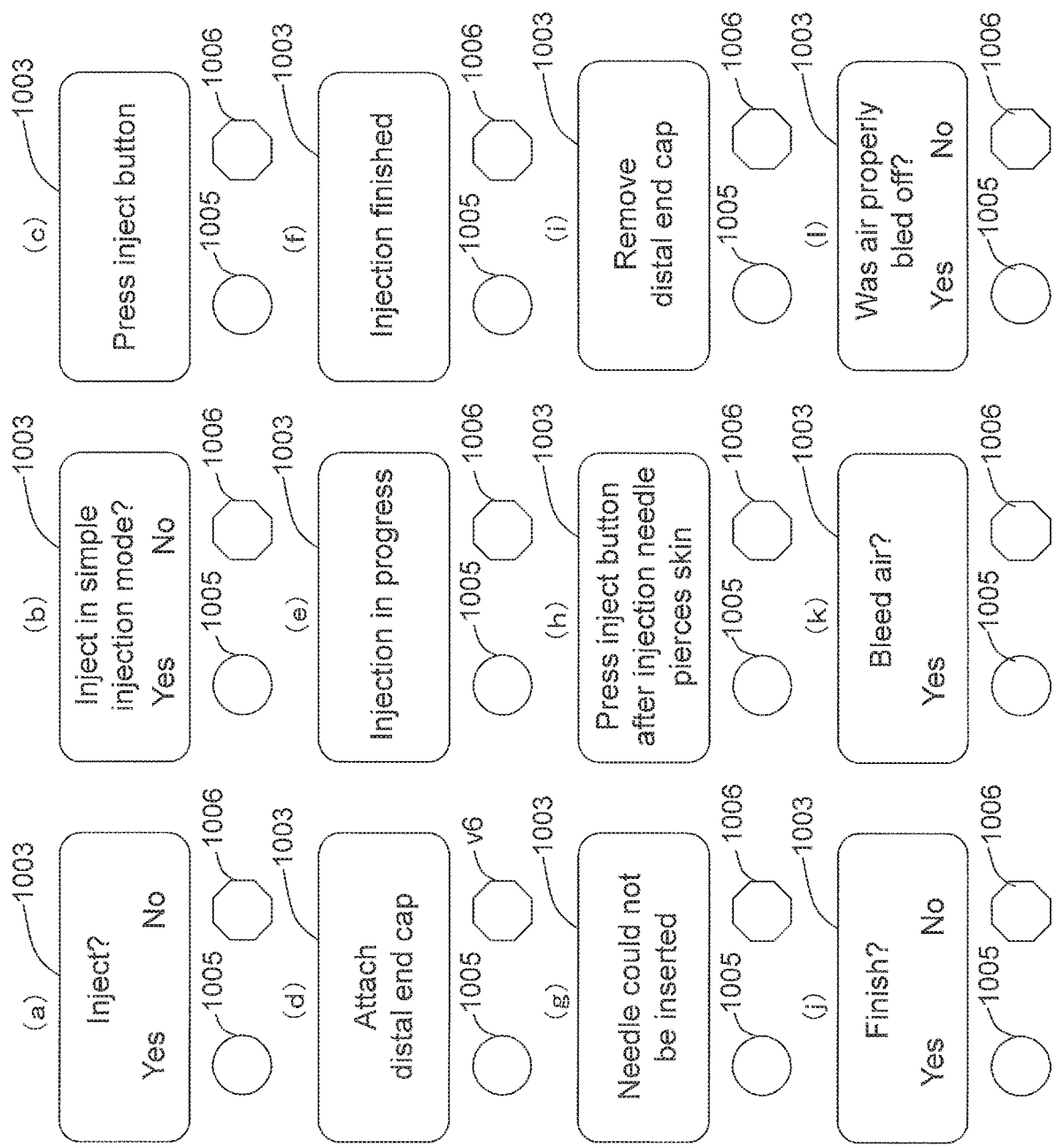
FIG. 36 is a diagram of the display of the display component of the pharmaceutical injection device in FIG. 31.

FIGS. 37 to 40 are flowcharts illustrating the operation of the pharmaceutical injection device in this embodiment. FIG. 36 shows an example of the display during the operation shown in FIGS. 37 to 40.

2-1. Normal Pharmaceutical Injection Mode

First, we will describe the normal pharmaceutical injection mode, in which pharmaceutical injection is executed in the normal way.

Figure 31:
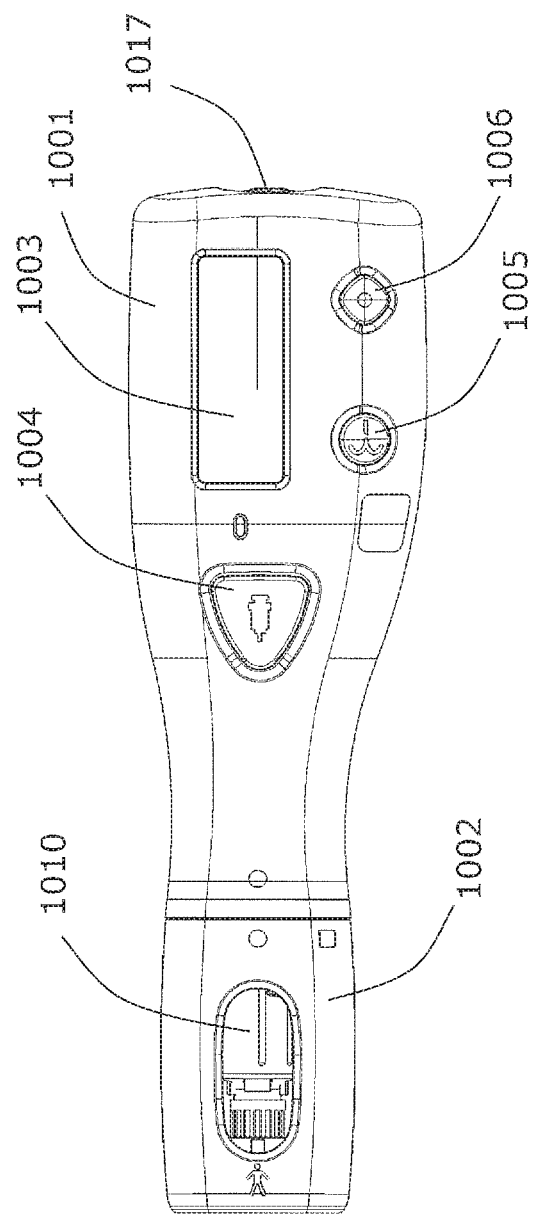
FIG. 31 is a front view of the pharmaceutical injection device pertaining to an embodiment of the present invention (needle home position)
Figure 37:
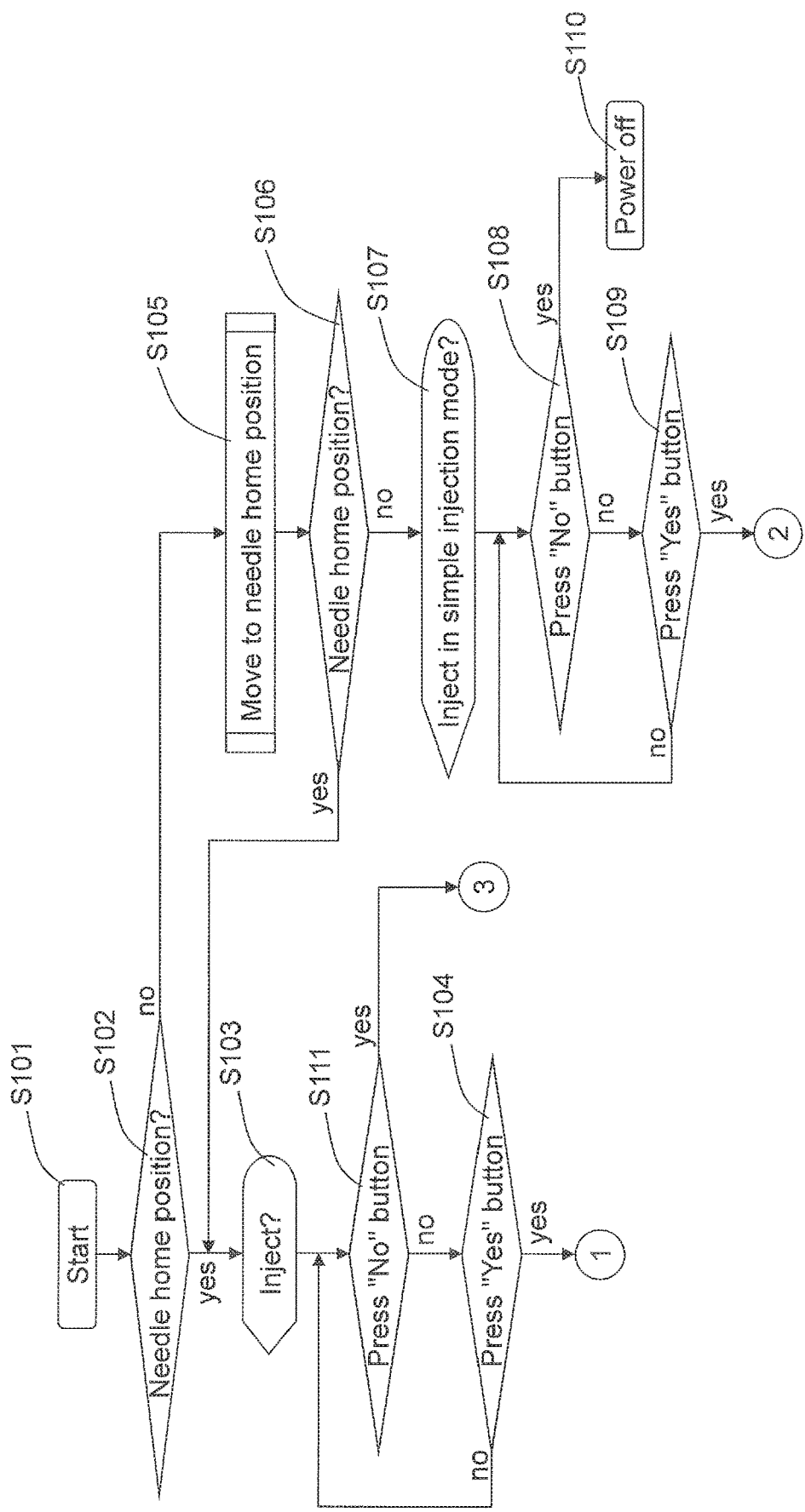
FIG. 37 is an operational flowchart of the pharmaceutical injection device in FIG. 31.

When pharmaceutical injection is performed from the state shown in FIG. 31, the power button 1017 is pushed by the user (S101 in FIG. 37).

The controller 1016 then uses the sensor 1018 to detect whether or not the injection needle 1014, the pharmaceutical syringe unit 1010, and the pharmaceutical syringe attachment component 1007 (including the inner case 1012) have returned to their home positions. If these are disposed at their home positions, the display component 1003 then displays a message of "Inject?" as shown in FIG. 36a (S102 and S103 in FIG. 37).

The user checks this display, and then operates the Yes button 1005 (S104 in FIG. 37).

Figure 38:
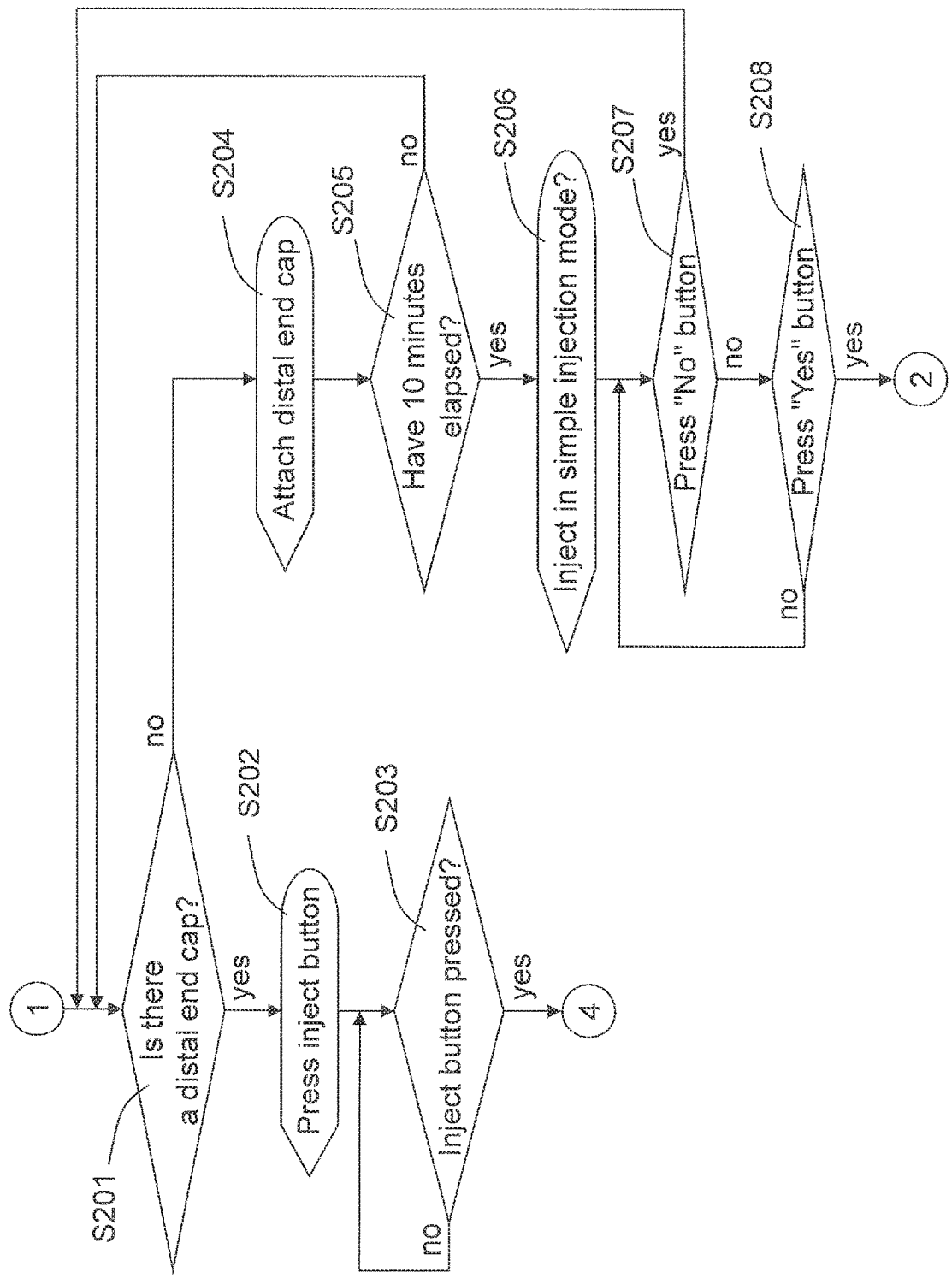
FIG. 38 is an operational flowchart of the pharmaceutical injection device in FIG. 31.

The controller 1016 then uses the sensor 1020 to detect whether or not the distal end cap 1002 has been attached to the main body case 1001 as shown in FIG. 31 (S201 in FIG. 38).

In the state in FIG. 31, since the distal end cap 1002 is attached to the main body case 1001, the controller 1016 causes the display component 1003 to display a message of "Press inject button" as shown in FIG. 36c (S202 in FIG. 38).

The user sees this display and operates the inject button 1004 (S203 in FIG. 38).

Figure 39:
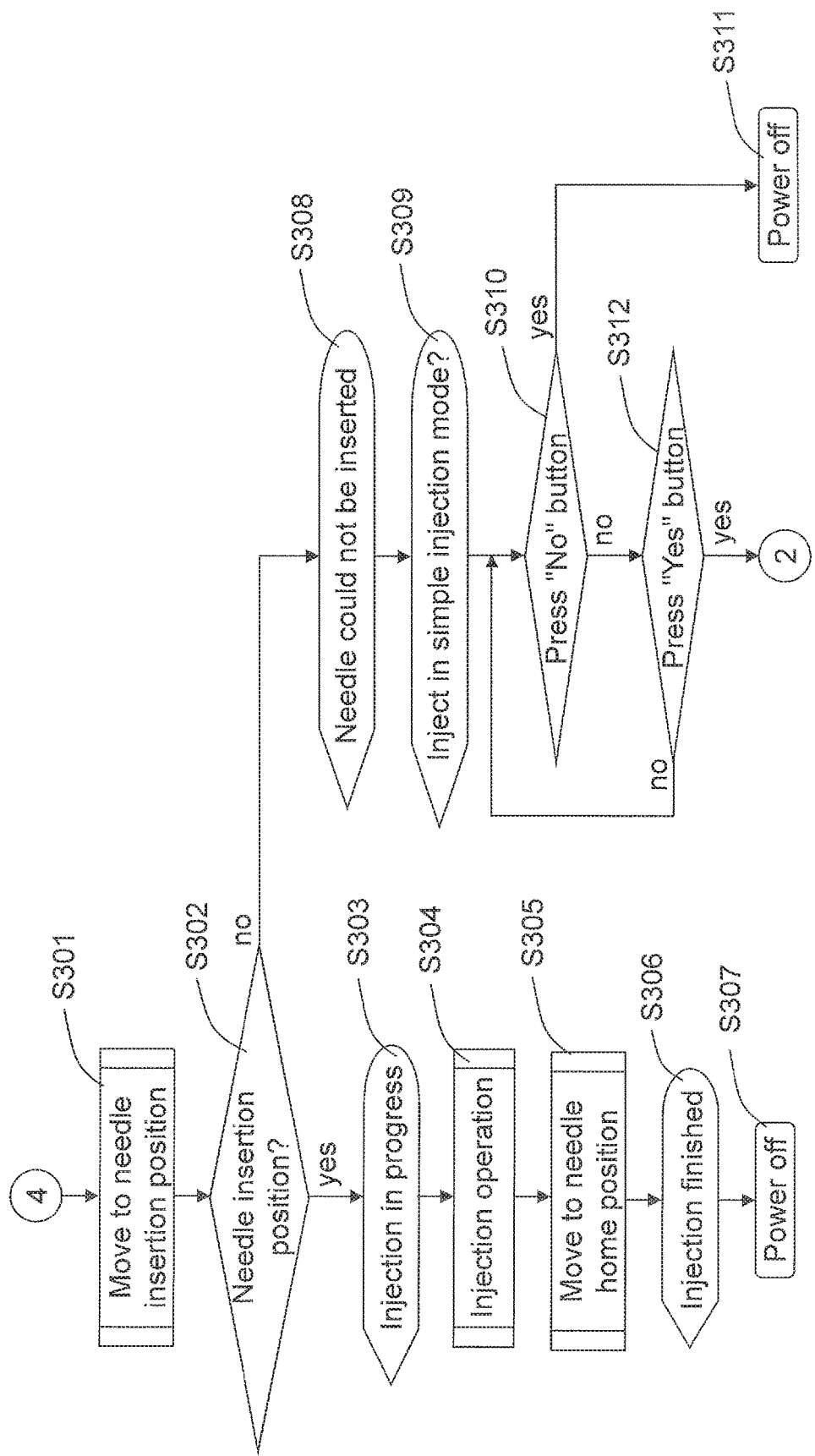
FIG. 39 is an operational flowchart of the pharmaceutical injection device in FIG. 31.

The first driver 1008 then moves the injection needle 1014 and the pharmaceutical syringe attachment component 1007 (including the inner case 1012) to the distal end side as shown in FIG. 32, and as a result, the injection needle 1014 sticks out to the distal end side from the distal end cap 1002, and pierces the skin (S301 in FIG. 39).

This state is detected by the sensor 1019 (S302 in FIG. 39), and the display component 1003 displays a message of "Injection is progress" as shown in FIG. 36e (S303 in FIG. 39).

In this state, the second driver 1009 moves the piston 1015 through the pharmaceutical syringe 1040 constituting the pharmaceutical syringe unit 1010 to the distal end side. Consequently, the pharmaceutical in the pharmaceutical syringe 1040 is injected through the injection needle 1014 into the body (S304 in FIG. 39).

After this, the controller 1016 reverses the drive of the first driver 1008. Consequently, the injection needle 1014, the pharmaceutical syringe unit 1010, and the pharmaceutical syringe attachment component 1007 (including the inner case 1012) are returned to the state in FIG. 31 (home positions). The sensor 1018 detects that they have returned to their home positions.

As shown in FIG. 36f, the controller 1016 causes the display component 1003 to display a message of "Injection finished," after which the power is switched off (S305, S306, and S307 in FIG. 39).

The above is the normal pharmaceutical injection operation, but various states will be described below.

2-2. Problem Detection in First Driver 1008 and Transition to Simple Pharmaceutical Injection Mode Next, the operation in the transition of the control flow to simple pharmaceutical injection mode when a malfunction of the first driver 1008 has been detected will be described.

First, in S102 in FIG. 37, if the injection needle 1014, the pharmaceutical syringe unit 1010, and the pharmaceutical syringe attachment component 1007 (including the inner case 1012) are not in the state in FIG. 31 (when they are not in their home positions in FIG. 31), the controller 1016 uses the first driver 1008 to return these to their home positions in FIG. 31 (S105 in FIG. 37).

When the sensor 1018 confirms that they have reached their home positions, the control moves on to S103 in FIG. 37 (S106 in FIG. 37).

On the other hand, if a return to the home positions cannot be detected in S106, the controller 1016 causes the display component 1003 to display a message of "Inject in simple pharmaceutical injection mode?" as shown in FIG. 36b (S107 in FIG. 37).

In this state, it is conceivable that, since the first driver 1008 is malfunctioning, for example, the pharmaceutical syringe attachment component 1007 (including the inner case 1012) and the pharmaceutical syringe unit 1010 and injection needle 1014 attached to the pharmaceutical syringe attachment component 1007 cannot be pushed forward. That is, if a return to the home position cannot be detected, it is conceivable that the injection needle 1014 will not be able to stick out to the distal end side from the distal end cap 1002 (see FIG. 32).

If the user wants to perform pharmaceutical injection after checking the display in S107 in FIG. 37, the Yes button 1005 is operated, and if the user does not want to perform pharmaceutical injection, the No button 1006 is operated (S108 and S109 in FIG. 37).

Figure 40:
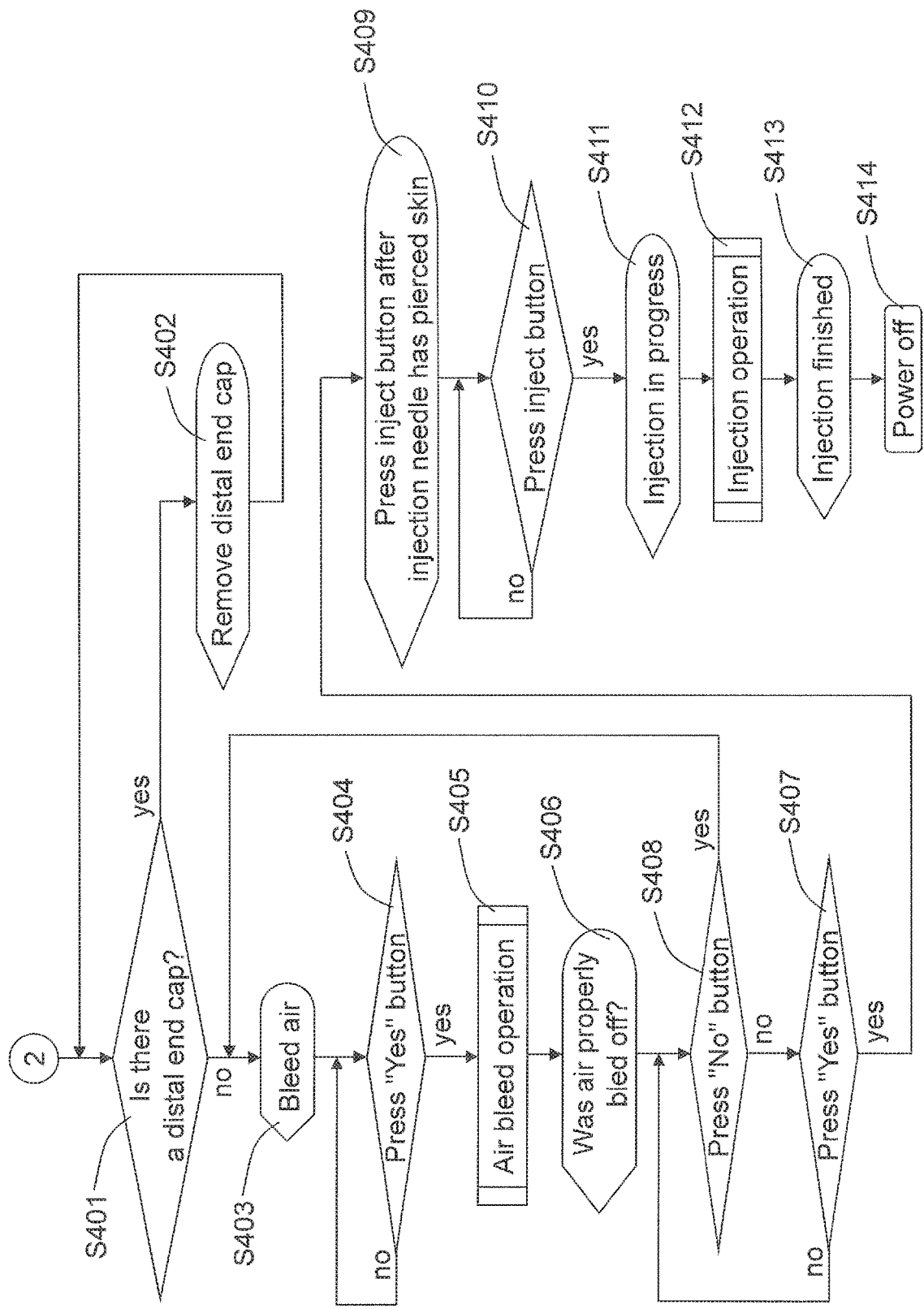
FIG. 40 is an operational flowchart of the pharmaceutical injection device in FIG. 31.

Here, if the Yes button 1005 is operated, the flow moves to S401 in FIG. 40, and the control transitions to simple pharmaceutical injection mode.

If the user operates the No button 1006, the power to the pharmaceutical injection device is switched off and the operation ends (S110 in FIG. 37).

2-3. Simple Pharmaceutical Injection Mode

The operation in simple pharmaceutical injection mode will now be described through reference to FIG. 40. This simple pharmaceutical injection mode is an operation in which an attempt is made to inject the pharmaceutical even in a state in which the first driver 1008 cannot make the injection needle 1014 pierce the skin.

In this case, first the sensor 1020 detects whether or not the distal end cap 1002 has been removed from the main body case 1001 as in FIG. 33 (S401 in FIG. 40).

At this point, if the sensor 1020 has detected that the distal end cap 1002 is still attached, the controller 1016 causes the display component 1003 to display a message of "Remove distal end cap" as shown in FIG. 36i, and thus prompts the user to remove the distal end cap 1002 (S402 in FIG. 40).

When the sensor 1020 detects that the distal end cap 1002 has been removed from the main body case 1001 as in FIG. 33 (from the state in FIG. 31), the controller 1016 causes the display component 1003 to display a message of "Bleed off air" as in FIG. 36k (S403 in FIG. 40).

That is, an air bleed operation is executed to confirm whether or not the second driver 1009 is in a state that allows safe operation, in a state in which the first driver 1008 is malfunctioning.

Therefore, the user operates the Yes button 1005, which executes an air bleed operation (S404 and S405 in FIG. 40).

In this air bleed operation, the second driver 1009 pushes the piston 1015 slightly to the distal end side, and this causes the pharmaceutical in the pharmaceutical syringe to squirt out from the injection needle 1014. The user confirms this squirting of the pharmaceutical to confirm that the air bleed operation has been performed.

Then, the controller 1016 causes the display component 1003 to display a message of "Was air properly bled off?" as shown in FIG. 36*l* (S406 in FIG. 40).

Since the user has already confirmed that the pharmaceutical squirted out of the injection needle 1014, he operates the Yes button 1005 (S407 in FIG. 40).

If it cannot be confirmed that the pharmaceutical has squirted out of the injection needle 1014, the No button 1006 is operated, and the control at this point returns to S403 in FIG. 40 (S408 in FIG. 40).

In S406 in FIG. 40, if the Yes button 1005 is operated, the controller 1016 causes the display component 1003 to display a message of (Press inject button after needle pierces skin" as shown in FIG. 36*h* (S409 in FIG. 40).

Upon seeing this display, the user pierces his skin with the injection needle 1014 in a state in which the injection needle 1014 is exposed as in FIG. 33, and then operates the inject button 1004 (S410 in FIG. 40).

The controller 1016 then causes the display component 1003 to display a message of "Injection in progress" as shown in FIG. 36*e*, and the pharmaceutical injection operation is executed (S411 and S412 in FIG. 40).

The pharmaceutical injection operation is an operation in which the second driver 1009 causes the piston 1015 to move to the distal end side through the pharmaceutical syringe 1040 constituting the pharmaceutical syringe unit 1010, and this causes the pharmaceutical in the pharmaceutical syringe 1040 to be injected through the injection needle 1014 into the body.

When this injection operation is finished, the controller 1016 causes the display component 1003 to display a message of "Injection finished" as shown in FIG. 36*f*, and then the power is switched off (S413 and S414 in FIG. 40).

2-4. Transition to Simple Pharmaceutical Injection Mode after Confirmation of Trouble in Pharmaceutical Injection Assistance Components We will now described the transition of the control flow to simple pharmaceutical injection mode in a state in which the injection needle 1014, the pharmaceutical syringe unit 1010, and the pharmaceutical syringe attachment component 1007 (including the inner case 1012) have returned to their home positions, but the user has already recognized trouble in the pharmaceutical injection assistance components (malfunction of the first driver 1008, or loss or breakage of the distal end cap 1002).

What happens when the No button 1006 is operated in the state of S103 in FIG. 37 (S111 in FIG. 37) will be described through reference to FIG. 41.

Figure 41:
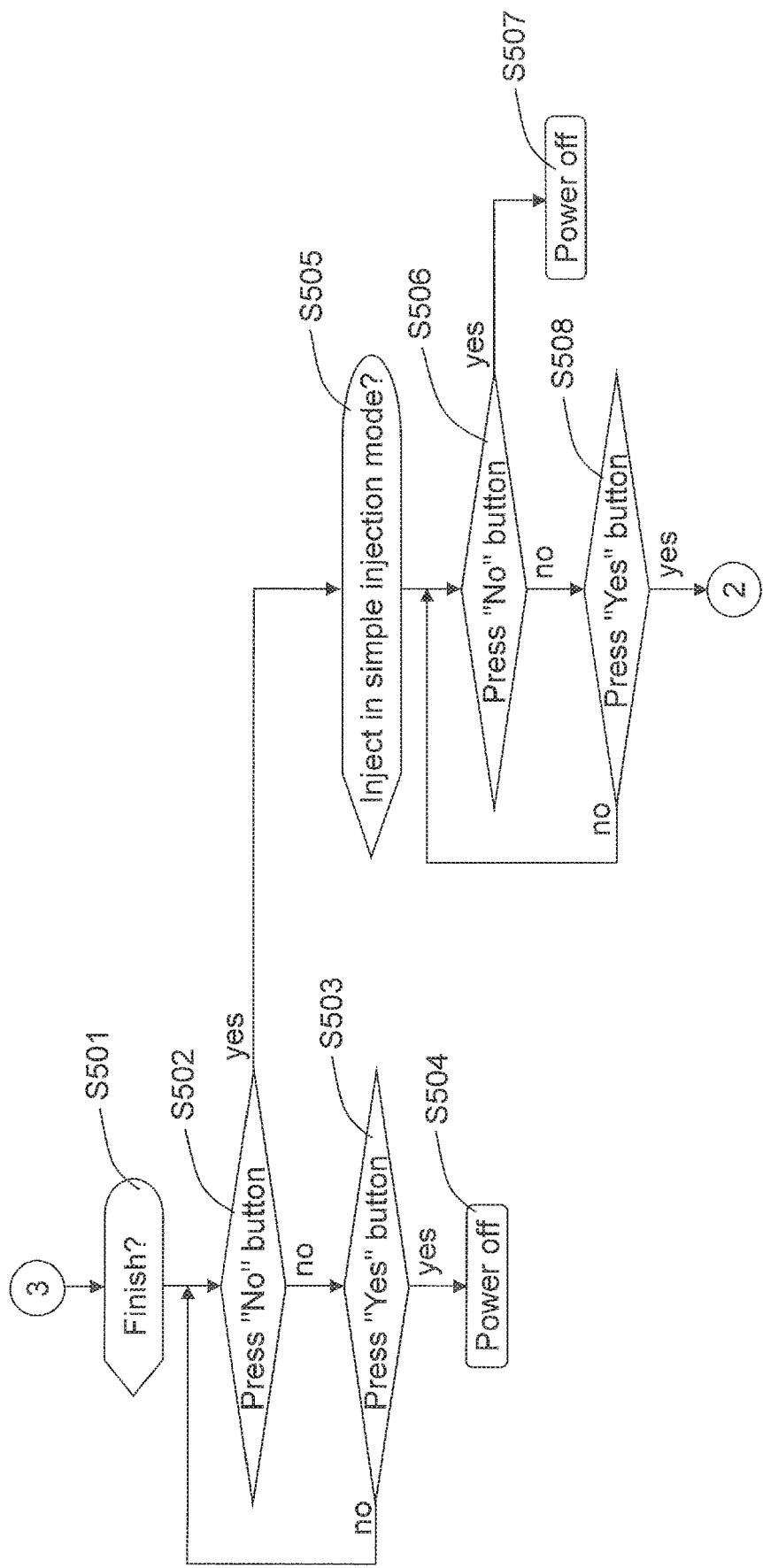
FIG. 41 is an operational flowchart of the pharmaceutical injection device in FIG. 31.

First, the controller 1016 causes the display component 1003 to display a message of "Finish?" as shown in FIG. 36*j* (S501 in FIG. 41).

The user checks this display, operates the Yes button 1005 to stop the pharmaceutical injection, and operates the No button 1006 to execute the simple pharmaceutical injection mode (S502 and S503 in FIG. 41).

Here, if the Yes button 1005 is operated, the controller 1016 switches off the power and ends control (S504 in FIG. 41).

If the No button 1006 is operated here, the controller 1016 causes the display component 1003 to display a message of "Inject in simple injection mode?" as shown in FIG. 36*b* (S505 in FIG. 41).

In contrast, the user operates the No button 1006 if a simple injection operation is not to be performed. As a result of this operation, the controller 1016 switches off the power and ends control (S506 and S507 in FIG. 41).

At this point, the Yes button 1005 is operated to perform a simple injection operation, and the flow moves to S401 in FIG. 40 and transitions to simple injection mode (S508 in FIG. 41).

This simple injection operation in which only the second driver 1009 is driven is also performed when the first driver 1008 malfunctions and the needle has returned to its home position, but the injection needle 1014, the pharmaceutical syringe unit 1010, and the pharmaceutical syringe attachment component 1007 (including the inner case 1012) cannot be moved to the distal end side. This simple injection operation in which only the second driver 1009 is driven is also performed when it is confirmed ahead of time that the distal end cap 1002 has been lost or damaged.

2-5. Transition to Simple Pharmaceutical Injection Mode when Distal End Cap 1002 is not Attached Next, we will describe the transition to control of the simple pharmaceutical injection mode in a state in which the normal pharmaceutical injection mode cannot be executed because the distal end cap 1002 has been lost, the distal end cap 1002 has been damaged, etc.

In S201 in FIG. 38, if the sensor 1020 detects that the distal end cap 1002 has not been attached to the main body case 1001, the controller 1016 causes the display component 1003 to display a message of "Attach distal end cap" as shown in FIG. 36*d*, and the user is thus prompted to attach the distal end cap 1002 (S204 in FIG. 38).

The controller 1016 uses the timer 1027 to monitor the attachment of the distal end cap 1002 for a specific length of time (S205 in FIG. 38).

That is, S201, S204, and S205 in FIG. 38 are repeated until a specific length of time has elapsed (10 minutes in the example shown in S205 in FIG. 38).

If the distal end cap 1002 was attached to the main body case 1001 during this time, the controller 1016 causes the display component 1003 to display a message of "Press inject button" as shown in FIG. 36*c*, and executes the operation in normal pharmaceutical injection mode.

On the other hand, if the attachment of the distal end cap 1002 to the main body case 1001 was not detected within the above-mentioned length of time, the controller 1016 causes the display component 1003 to display a message of "Inject in simple injection mode?" as shown in FIG. 36*b* (S206 in FIG. 38).

After checking this display, if user does not want to perform the simple injection operation, the user operates the No button 1006, and the flow moves on to checking the attachment of the distal end cap 1002 (S207 in FIG. 38).

If the user want to perform the simple injection operation, the user operates the Yes button 1005, the flow moves to S401 in FIG. 40, and control changes to simple injection mode (S208 in FIG. 38).

This simple pharmaceutical injection mode is executed when the distal end cap 1002 is broken, or if the distal end cap 1002 has been lost.

In the normal injection mode, the attachment of the distal end cap 1002 to the main body case 1001 is a condition for driving the first driver 1008. Accordingly, if the distal end cap 1002 should be broken or lost, the distal end cap 1002 cannot be attached to the main body case 1001, so it will be impossible for the sensor 1020 to detect the attachment of the distal end cap 1002 to the main body case 1001, and the first driver 1008 cannot be actuated.

Thus, the attachment of the distal end cap 1002 is a condition of the actuation of the first driver 1008 in a normal injection operation. This is because in a normal injection operation, the first driver 1008 attempts to move the inner case 1012 and the injection needle 1014 to the distal end side so that the needle pierces the skin, but if there is no distal end cap 1002, the distal end of the pharmaceutical injection device cannot properly come into contact with the skin, so proper piercing is impossible.

Thus, in a normal injection operation, the pharmaceutical cannot be injected if the distal end cap 1002 has not been mounted, but in a simple pharmaceutical injection mode (2-3), as discussed above, the pharmaceutical can be injected without operating the first driver 1008.

Specifically, since the needle insertion operation is not performed by the pharmaceutical injection device in the simple pharmaceutical injection mode, the injection of the pharmaceutical is performed by the pharmaceutical injection device after the user has inserted the needle.

2-6. Detection of Trouble in First Driver 1008, and Transition to Simple Pharmaceutical Injection Mode Next, we will describe the transition of the control flow to the simple pharmaceutical injection mode when a malfunction of the first driver 1008 has been detected. In section 2-2, trouble with the first driver 1008 is detected from the fact that the injection needle 1014, etc., is not disposed at its home position, but in this section 2-6, trouble with the first driver 1008 is detected from the fact that movement from the home position to the needle insertion position is impossible.

In S301 in FIG. 39, the first driver 1008 moves the needle to the insertion position, but since the sensor 1019 at this point cannot detect this movement to the needle insertion position (S302 in FIG. 39), the controller 1016 causes the display component 1003 to display a message of "Needle could not be inserted" as shown in FIG. 36g, and the user is notified of trouble with the needle insertion operation (S308 in FIG. 39).

This indicates whether malfunction of the first driver 1008 has occurred during a normal pharmaceutical injection operation, or that the needle insertion operation failed for some other reason.

After the display in FIG. 36g has continued for a certain length of time, the controller 1016 causes the display component 1003 to display a message of "Inject in simple injection mode?" as shown in FIG. 36b (S309 in FIG. 39).

If, in response to this display, the user does not want to perform a needle insertion operation, he operates the No button 1006, and as a result the controller 1016 switches off the power and ends control (S310 and 5311 in FIG. 39).

On the other hand, if the user wants to perform a simple injection operation is to be performed, the user operates the Yes button 1005 (S312 in FIG. 39), and the control moves on to S401 in FIG. 40 and goes into simple injection mode.

3. Main Features

3-1

The pharmaceutical injection device in the above embodiment comprises the main body case 1001, the distal end cap 1002, the first driver 1008, the second driver 1009, the attached state detector 1030, and the controller 1016. The main body case 1001 has the pharmaceutical syringe attachment component 1007 on the distal end side. The distal end cap 1002 can be removably attached to the distal end side of the main body case 1001. The first driver 1008 moves the pharmaceutical syringe unit 1010 attached to the pharmaceutical syringe attachment component 1007 to the distal end side or the rear side. The second driver 1009 moves the gasket 1041 of the pharmaceutical syringe 1040 constituting the pharmaceutical syringe unit 1010 to the distal end side. The attached state detector 1030 detects the attached state of the distal end cap 1002 to the main body case 1001. In pharmaceutical injection, the controller 1016 is able to execute the normal pharmaceutical injection mode, in which the first driver 1008 and the second driver 1009 are actuated, when the attached state detector 1030 has detected that the distal end cap 1002 has been attached to the main body case 1001, and to execute the simple pharmaceutical injection mode, in which only the second driver 1009 is actuated, when the attached state detector 1030 has detected a state in which the distal end cap 1002 has not been attached to the main body case 1001.

Thus, a feature of the pharmaceutical injection device in this embodiment is that it has a simple injection operation mode in which only the second driver 1009 is actuated and only the pharmaceutical injection operation is performed in the event that a normal needle insertion operation, injection operation, or needle removal operation cannot be performed due to loss of or damage to the distal end cap 1002, etc.

Accordingly, even if the distal end cap 1002 is lost, pharmaceutical injection can still be carried out by executing the simple pharmaceutical injection mode in which only the second driver 1009 is actuated, after the attached state detector 1030 has detected a state in which the distal end cap 1002 is not attached to the main body case 1001. This minimizes the effect caused by problems such as a lost cap, and makes the device extremely convenient to use.

3-2

Also, the pharmaceutical injection device in the above embodiment comprises the main body case 1001, the distal end cap 1002, the first driver 1008, the second driver 1009, the sensor 1018 or the sensor 1019 (an example of an operating state detector), and the controller 1016. The main body case 1001 has the pharmaceutical syringe attachment component 1007 on the distal end side. The distal end cap 1002 can be removably attached to the distal end side of the main body case 1001. The first driver 1008 moves the pharmaceutical syringe unit 1010 attached to the pharmaceutical syringe attachment component 1007 to the distal end side or the rear side. The second driver 1009 moves the gasket 1041 of the pharmaceutical syringe 1040 constituting the pharmaceutical syringe unit 1010 to the distal end side. The sensor 1018 or the sensor 1019 detects the operating state of the first driver 1008. In pharmaceutical injection, the controller 1016 is able to execute the simple pharmaceutical injection mode, in which only the second driver 1009 is actuated, when the sensor 1018 or the sensor 1019 has detected that the first driver 1008 is not operating properly.

Thus, a feature of the pharmaceutical injection device in this embodiment is that it has a simple injection operation mode, in which just the second driver 1009 may be driven and just the pharmaceutical injection operation may be performed even if malfunction or the like of the first driver 1008 should preclude the normal needle insertion operation, injection operation, or needle removal operation.

Accordingly, even if some trouble occurs in the first driver 1008, pharmaceutical injection can still be carried out by executing a simple pharmaceutical injection mode, in which only the second driver 1009 is actuated, after the attached state detector 1030 has detected that the distal end cap 1002 has not been attached to the main body case 1001. This minimizes the effect caused by problems such as a malfunction, and makes the device extremely convenient to use.

4. Other Embodiments

A

In the above embodiment, even if it is detected in S201 that the distal end cap 1002 has not been attached, whether or not the distal end cap 1002 has been attached is determined again in S401 in the execution of the simple pharmaceutical injection mode, but this determination does not have to be done again if it was determined in S201 that the distal end cap 1002 was not attached.

B

In the above embodiment, the system waits for 10 minutes in S205, but if it has already been recognized that the distal end cap 1002 has been lost, the user may select to skip this 10-minute wait.

C

In the above embodiment, in executing the simple pharmaceutical injection mode, an air bleed operation is performed, but it should go without saying that the air bleed operation may be performed in the execution of the normal pharmaceutical injection mode as well.

INDUSTRIAL APPLICABILITY

The pharmaceutical injection device may be extremely convenient to use because the attachment of the injection needle to the pharmaceutical syringe unit, or the removal of the injection needle from the pharmaceutical syringe unit, can be executed even though the distal end cap has not been removed from the main body case.

Therefore, this device is expected to find wide application in the field of various kinds of pharmaceutical injection device, etc.

Also, with the pharmaceutical injection device, pharmaceutical injection may be be carried out even if some kind of trouble should occur in the components that assist pharmaceutical injection, so this device is expected to find wide application in the field of insulin, growth hormone, and various other such pharmaceutical injection devices, etc.

The invention claimed is:

1. A pharmaceutical injection device, comprising:
a main body case having a pharmaceutical syringe attachment component on a distal end side;
a distal end cap removably attached to the distal end side of the main body case;
a first driver configured to move the pharmaceutical syringe attachment component and a pharmaceutical syringe unit attached to the pharmaceutical syringe attachment component toward or away from the distal end side of the main body case;
a second driver configured to move a gasket of a pharmaceutical syringe to the distal end side of the main body case; and
a controller that is connected to the first driver and the second driver,
wherein the controller is configured to use the first driver to move the pharmaceutical syringe unit to a needle operation position at which at least part of a large-diameter part on a rear side of a needle case covering an injection needle is exposed outside beyond a distal end opening in the distal end cap in a state in which the needle case has been attached to the pharmaceutical syringe unit.

2. The pharmaceutical injection device according to claim 1, wherein the large-diameter part is knurled.

3. The pharmaceutical injection device according to claim 1, wherein, after the pharmaceutical in a pharmaceutical syringe has been injected, the controller is configured to use the first driver to retract the pharmaceutical syringe unit to a needle removal position, which serves as an attachment position for attaching the needle case covering the injection needle to the pharmaceutical syringe unit.

4. The pharmaceutical injection device according to claim 3, Wherein, after attachment of the needle case, the controller is configured to use the first driver to move the pharmaceutical syringe attachment component to the needle operation position from the needle removal position.

5. The pharmaceutical injection device according to claim 1, wherein the pharmaceutical syringe unit includes a first detection member configured to detect attachment to the pharmaceutical syringe unit of a needle base to which the injection needle is attached.

6. The pharmaceutical injection device according to claim 1, wherein the pharmaceutical syringe unit includes a second detection member configured to detect that the needle case covering the injection needle has been attached to the pharmaceutical syringe unit.

7. The pharmaceutical injection device according to claim 1, further comprising the pharmaceutical syringe unit that has been attached to the pharmaceutical syringe attachment component.

8. The pharmaceutical injection device according to claim 1, further comprising:
a first detector configured to detect attachment of the injection needle to the pharmaceutical syringe unit; and
a second detector configured to detect attachment of the needle case covering the injection needle to the pharmaceutical syringe unit,
wherein the controller is configured to retract the pharmaceutical syringe unit to a needle removal position after detection of the attachment of the needle case and the injection needle at the needle operation position when the injection needle is attached to the pharmaceutical syringe unit.

9. The pharmaceutical injection device according to claim 1, further comprising a second detector configured to detect attachment of the needle case covering the injection needle to the pharmaceutical syringe unit,
wherein, in removal of the injection needle from the pharmaceutical syringe unit, the controller is configured to use the first driver to retract the pharmaceutical syringe attachment component to a needle removal position before moving to the needle operation position, and move the pharmaceutical syringe unit to the needle operation position after detection of the attachment of the needle case at the needle removal position.

10. The pharmaceutical injection device according to claim 1, wherein the controller is configured to move the pharmaceutical syringe unit to the needle operation position in a state in which the distal end cap has been attached to the main body case.

11. A pharmaceutical injection device, comprising:
a main body case having a pharmaceutical syringe attachment component on a distal end side;
a distal end cap that can be removably attached to the distal end side of the main body case, the distal end cap being configured to be pressed against a subject during needle insertion, the distal end cap including an opening through which a needle projects during needle insertion;
a first driver configured to move a pharmaceutical syringe unit attached to the pharmaceutical syringe attachment component toward or away from the distal end side of the main body case;
a second driver configured to move a gasket of a pharmaceutical syringe to a side of the opening;
an attached state detector configured to detect attachment of the distal end cap to the main body case; and
a controller that, when the attached state detector has detected a state in which the distal end cap has been attached to the main body case, is configured to execute a normal pharmaceutical injection mode in which the first driver and the second driver are actuated, and, when the attached state detector has detected a state in which the distal end cap has not been attached to the main body case, is configured to execute a simple pharmaceutical injection mode in which only the second driver is actuated,
wherein the controller is configured to use the first driver to move the pharmaceutical syringe unit to a needle operation position at which at least part of a large-diameter part on a rear side of a needle case covering an injection needle is exposed outside beyond the opening in the distal end cap in a state in which the needle case has been attached to the pharmaceutical syringe unit.

12. The pharmaceutical injection device according to claim 11, wherein, during execution of the simple pharmaceutical injection mode, the controller is configured to cause the attached state detector to detect non-attachment of the distal end cap, and then use the second driver to perform an air bleed operation, after which the second driver is driven to inject a pharmaceutical.

13. The pharmaceutical injection device according to claim 11, further comprising a display component that is connected to the controller,
wherein the controller is configured to cause the display component to give a display related to the simple pharmaceutical injection mode during execution of the simple pharmaceutical injection mode.

14. The pharmaceutical injection device according to claim 13, wherein the controller is configured to cause the display component to give another display for selecting an execution of pharmaceutical injection in the simple pharmaceutical injection mode.

15. A pharmaceutical injection device, comprising:
a main body case having a pharmaceutical syringe attachment component on a distal end side;
a distal end cap that can be removably attached to the distal end side of the main body case;
a first driver configured to move the pharmaceutical syringe attachment component and a pharmaceutical syringe unit attached to the pharmaceutical syringe attachment component toward or away from the distal end side of the main body case;
a second driver configured to move a gasket of a pharmaceutical syringe to a side of an opening in the distal end cap;
an operating state detector configured to detect an operating state of the first driver; and
a controller that, during pharmaceutical injection, is configured to execute a simple pharmaceutical injection mode in which only the second driver is actuated when the operating state detector has detected that the first driver is not operating properly,
wherein the controller is configured to use the first driver to move the pharmaceutical syringe unit to a needle operation position at which at least part of a large-diameter part on a rear side of a needle case covering an injection needle is exposed outside beyond the opening in the distal end cap in a state in which the needle case has been attached to the pharmaceutical syringe unit.

* * * * *